US005693774A

United States Patent [19]

Schupp et al.

[11] Patent Number: 5,693,774

[45] Date of Patent: Dec. 2, 1997

[54] DNA SEQUENCES INVOLVED IN SORAPHEN BIOSYNTHESIS BY MYXOBACTERIA

[75] Inventors: Thomas Schupp, Möhlin; Snezana Neff, Bubendorf; James M. Ligon, Basel, all of Switzerland

[73] Assignee: Novartis Finance Corporation, New York, N.Y.

[21] Appl. No.: 392,731

[22] PCT Filed: Aug. 24, 1993

[86] PCT No.: PCT/US93/07954

§ 371 Date: Feb. 24, 1995

§ 102(e) Date: Feb. 24, 1995

[87] PCT Pub. No.: WO94/05793

PCT Pub. Date: Mar. 17, 1994

[51] Int. Cl.$^6$ .................................................... C07H 21/04

[52] U.S. Cl. ...................................... 536/23.1; 536/24.32

[58] Field of Search ......................... 435/6, 252.3, 320.1; 536/23.1, 24.32

[56] References Cited

U.S. PATENT DOCUMENTS 4,935,340 6/1990 Baltz et al. ................................ 435/6

FOREIGN PATENT DOCUMENTS 0358606 3/1990 European Pat. Off. ......... C07H 19/01
0472494 8/1991 European Pat. Off. ......... C12N 15/52
0501921 2/1992 European Pat. Off. ......... C12N 15/74
WO87/03907 12/1986 WIPO ............................ C12N 15/00
WO94/05793 8/1993 WIPO ............................ C12N 15/52

OTHER PUBLICATIONS

Malpartida et al. (1987) Nature 325:818–821.
Sherman et al. (1989) *EMBO J.* 8:2717–2725.
Furuichi et al. (1985) *J. Bacteriol.* 164:270–5.
Kuspa et al. (1989) *Proc. Natl. Acad. Sci. USA* 86:8917–21.
Chen et al. (1991) *J. Bacteriol.* 173:2109–15.
Kimsey et al. (1991) *J. Bacteriol.* 173:6790–7.
He et al. (1994) *Proc. Natl. Acad. Sci. USA* 91:9584–7.
Schupp et al. (1995) *J. Bacteriol.* 177:3673–9.
Pospiech et al. (1995) *Microbiology* 141:1793–1803.
Jaoua et al. (1992) *Plasmid* 28:157–65.
Gerth et al. (1994) *J. Antibiot.* 47:23–31.

*Primary Examiner*—W. Gary Jones
*Assistant Examiner*—Amy Atzel
*Attorney, Agent, or Firm*—J. Timothy Meigs

[57] ABSTRACT

The present invention relates to a DNA molecule isolated from the genome of *Sorangium cellulosum* that encodes a polypeptide required for soraphen biosynthesis and to methods for the preparation of said DNA fragment. The present invention further relates to plasmids, vectors, and host cells that comprise the DNA molecule of the invention.

10 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 784 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Sorangium cellulosum ( v i i ) IMMEDIATE SOURCE:
( B ) CLONE: Cosmid clone p98/1

( i x ) FEATURE:
( A ) NAME/KEY: misc_feature
( B ) LOCATION: 1..784
( D ) OTHER INFORMATION: /product="Constituent of the ' soraphen gene cluster'"

( x i ) SEQUENCE DESCRIPTION: SEQ ID NO:1:

```
GTCGACTACG CCTCCCACTC CGCCCAGATG GACGCCGTCC AAGACGAGCT CGCCGCAGGT    60
CTAGCCAACA TCGCTCCTCG GACGTGCGAG CTCCCTCTTT ATTCGACCGT CACCGGCACC   120
```

-continued

```
AGGCTCGACG GCTCCGAGCT CGACGGCGCG TACTGGTATC GAAACCTCCG GCAAACCGTC    180
CTGTTCTCGA GCGCGACCGA GCGGCTCCTC GACGATGGGC ATCGCTTCTT CGTCGAGGTC    240
AGCCCCCATC CCGTGCTCAC GCTCGCCCTC CGCGAGACCT GCGAGCGCTC ACCGCTCGAT    300
CCCGTCGTCG TCGGCTCCAT TCGACGCGAC GAAGGCCACC TCGCCCGCCT GCTCCTCTCC    360
TGGGCGGAGC TCTCTACCCG AGGCCTCGCG CTCGACTGGA ACGCCTTCTT CGCGCCCTTC    420
GCTCCCCGCA AGGTCTCCCT CCCCACCTAC CCCTTCCAAC GCGAGCGCTT CTGGCTCGAC    480
GCCTCCACGG CGCACGCTGC CGACGTCGCC TCCGCAGGCC TGACCTCGGC CGACCACCCG    540
CTGCTCGGCG CCGCCGTCGC CCTCGCCGAC CGCGATGGCT TTGTCTTCAC AGGACGGCTC    600
TCCCTCGCAG AGCACCCGTG GCTCGAAGAC CACGTCGTCT TCGGCATACC CGTCCTGCCA    660
GGCGCCGCCC TCCTCGAGCT CGCCCTGCAT GTCGCCCATC TCGTCGGCCT CGACACCGTC    720
GAAGACGTCA CGCTCGACCC CCCCCTCGCT CTCCCATCGC AGGGCGCCGT CCTCCTCCAG    780
ATCT                                                                 784
```

( 2 ) INFORMATION FOR SEQ ID NO:2:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="synthetic oligonucleotide Oli1"

( i i i ) HYPOTHETICAL: NO ( x i ) SEQUENCE DESCRIPTION: SEQ ID NO:2:

```
TACTGGTATC GAAACCT                                                    17
```

( 2 ) INFORMATION FOR SEQ ID NO:3:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="synthetic oligonucleotide Oli2"

( i i i ) HYPOTHETICAL: NO ( x i ) SEQUENCE DESCRIPTION: SEQ ID NO:3:

```
GAAGACGACG TGGTCTT                                                    17
```

DNA SEQUENCES INVOLVED IN SORAPHEN BIOSYNTHESIS BY MYXOBACTERIA

FIELD OF THE INVENTION

The present invention relates to the area of recombinant DNA technology and in particular to the application thereof to myxobacteria, but preferably to myxobacteria of the Sorangium/Polyangium group, for the localization, identification and cloning of individual genes and even of entire gene clusters within the bacterial genome.

BACKGROUND OF THE INVENTION

The myxobacteria of the Sorangium/Polyangium group are highly specialized organisms which are frequently detectable in soil samples, dead plant material or in animal dung. Characteristic of this group of microorganisms is, inter alia, their ability to utilize cellulose or cellulose-containing degradation products as sole C source. Another characteristic feature of this group is their ability to produce highly active secondary metabolites.

To date, numerous strains of this group of organisms which are able, for example, to synthesize plant-microbicidal compounds have been described. Of particular importance in this connection are the so-called soraphens, whose structural particulars are described in detail, for example, in EP 0 358 606. The soraphens are macrocyclic compounds which have a cytostatic activity and a favorable biocidal spectrum against pathogenic microorganisms, but especially against phytopathogenic fungi. These compounds have very advantageous curative, systemic and, in particular, preventive properties and are therefore outstandingly suitable for use for the therapeutic treatment of mammalians and protecting numerous crop plants.

It is also known of other representatives of the group of myxobacteria that they are able to synthesize highly active compounds with antibiotic and cytostatic potency [Reichenbach et al (1988)]. Because of the pharmaceutical potential of these compounds and the importance, resulting therefrom, for plant protection, there is great interest in understanding the genetic bases of their synthesis in order thus to provide the possibility of being able to influence them specifically where appropriate.

This is desirable in particular because the natural producer strains, as also in the case of soraphen biosynthesis, very often provide the interesting secondary metabolites only in inadequate concentrations which are far from sufficient to satisfy the demand for substance for wider-ranging activity assays, to say nothing of commercial production.

Furthermore, these strains prove in many cases to be problematic and difficult to handle and therefore unsuitable for use on an industrial scale, for example in a fermentation process.

It would therefore be extremely desirable to decipher the genetic bases of secondary metabolite production in individual interesting representatives of the myxobacteria, because this opens up a large number of possibilities for intervening directly or indirectly in the synthetic process. Thus, for example, it would be conceivable to attempt to increase the productivity of the producer strains by targeted mutations or insertion of further gene copies. Another conceivable alternative relates to a possible transfer of the complete gene cluster which is responsible for secondary metabolite biosynthesis, or else selected parts thereof, into an organism strain which is optimized for production purposes and which can then be employed for metabolite production on the industrial scale.

However, the precondition for this is the provision of a method which makes it possible for these organisms to be subjected to direct and preferably targeted genetic manipulation using recombinant DNA techniques, for example by targeted incorporation of new genes or gene fragments or other DNA sequences, including whole plasmids, into the genome of the myxobacteria.

Individual representatives from the group of myxobacteria have already been the subject of investigations in this direction. Particular interest was directed in this connection primarily at *Myxococcus xanthus*, a myxobacterium which has to date already been rather well researched and for which various gene transfer methods have also already been described. Thus, for example, the coli phage P1 was initially utilized very intensively for investigations relating to the insertion of transposon Tn5 into the *Myxococcus xanthus* chromosome [Kaiser (1984); Kuner and Kaiser (1981)] and then subsequently also for transfer of genes cloned in *Myxococcus xanthus* back into the original *E. coli* host [O'Conner and Zusman (1983); Shimkets et al (1983)].

Another method for gene transfer is based on the use of the plasmid RP4 which has a very wide host range. Breton et al (1985) were able to show that this plasmid can be transferred via conjugation from *E. coli* to *Myxococcus xanthus* and there undergoes stable integration into the chromosome. Based on these properties, Breton et al (1986) and Breton and Guespin-Michel (1987) were able to integrate foreign genes into the chromosome of *Myxococcus xanthus*. As emerged from investigations by Jaoua et al (1987; 1989), the observed integration is very probably based on a so-called site specific recombination. The latter is thus confined to particular sites, which have a narrow spatial limitation, within the *Myxococcus xanthus* chromosome because it is mediated by one or more so-called hot spots on the RP4 plasmid. A transformation system of this type is, because of the structural limitations, very limited in its flexibility and therefore unsuitable for use within the scope of the present invention.

Furthermore, it has emerged in the course of the investigations carried out within the scope of this invention that the previously known Myxococcus system discussed here is not applicable to bacteria of the Sorangium/Polyangium group. It is assumed that these organisms lack the specific structural elements which are necessary for site specific recombination on their chromosomes. In addition, it has been found that no stable transposition, for example on use of transposon Tn5, takes place with these organisms either.

Pending EP-A No. 92810128.6 and Jaoua et al (1992) disclose for the first time a transformation system which makes possible direct and targeted genetic manipulation of representatives of the group of myxobacteria, but especially of myxobacteria of the Sorangium/Polyangium group, using recombinant DNA techniques and thus provides the preconditions for the identification and isolation, disclosed within the scope of this invention, of DNA fragments which comprise at least one gene or parts of a gene which are involved directly or indirectly in the biosynthesis of secondary metabolites, but especially in soraphen biosynthesis.

The object which is to be achieved within the scope of this invention thus primarily relates to the provision of a DNA fragment which comprises a DNA region which is involved directly or indirectly in the synthesis of secondary metabolites in myxobacteria and in this case preferably in myxobacteria of the Sorangium/Polyangium group, but especially in the synthesis of soraphen, and which comprises at least one of the involved genes or parts thereof, but preferably the totality of the DNA sequences responsible for the secondary metabolite synthesis.

It has already been known for a long time from earlier investigations, for example on actinomycetes, that genes which are involved directly or indirectly in the individual steps of secondary metabolite biosynthesis are, in the majority of cases known hitherto, organized in the form of gene clusters on the bacterial chromosome. By contrast, involvement of plasmid-bound genes has been detectable to date only in rare cases.

A number of procedures have been proposed to date for isolating genes whose gene products are involved indirectly or directly in antibiotic biosynthesis. These include, for example, the so-called complementation methods in the course of which it is attempted to restore, with the aid of fragments obtained from wild-type DNA, the synthetic ability of defective mutants which, because of a specific mutation, are no longer able to synthesize the required antibiotic [see, for example, Malpartida and Hopwood, 1984].

An alternative method for finding genes which are involved in the biosynthesis of polyketide antibiotics is described in WO 87/03907. This entails using a DNA fragment which comprises at least one part of a gene which is involved in the biosynthesis of a known polyketide antibiotic as DNA hybridization probe for screening a genomic gene bank which has previously been prepared from the genomic DNA of the interesting microorganism.

Although the principal techniques for the identification and isolation of such gene clusters are thus known, the applicability thereof to a novel organism group which has been but little investigated to date is, as a rule, problematic because of the uncertainties involved. This is particularly true when, as in the present case, there is no information available about the structural organization of the genome and therefore, in the search for the gene cluster responsible for the secondary metabolite biosynthesis, it is first necessary to find a suitable starting point for the necessary genome analysis. This is probably also the reason why the relatively modest information concerning the genetic structuring of secondary metabolite synthesis is to date concentrated on a few well-investigated organism groups, while next to nothing is known for others, such as, for example, the myxobacteria.

It has now been possible for the first time within the scope of the present invention, using the method described in EP-A No. 92810128.6 and Jaoua et al (1992), to locate within a myxobacterial genome a DNA region which is involved directly or indirectly in the biosynthesis of secondary metabolites and which is used as starting point for the identification and isolation of the gene cluster surrounding this region and subsequently to isolate and to clone the latter. The region is, in this connection, in particular one which can be obtained from the gene cluster, which is responsible for soraphen biosynthesis, within the genome of *S. cellulosum* and which is demonstrably involved in the biosynthesis of soraphen.

SUMMARY OF THE INVENTION

The present invention thus primarily relates to a DNA fragment which comprises a DNA region which is preferably obtainable from the gene cluster, which is responsible for soraphen biosynthesis, within the genome of *S. cellulosum* and which is involved directly or indirectly in the biosynthesis of soraphen, including the adjacent DNA regions on the right and left, which, because of their function in connection with soraphen biosynthesis, are revealed as constituents of the "soraphen gene cluster" and which can be identified with the aid of the previously isolated DNA fragment.

Preferred within the scope of this invention is a DNA fragment which comprises a DNA region which is obtainable from the "soraphen gene cluster" of *S. cellulosum* with the aid of the method described hereinafter.

A particularly preferred DNA fragment comprises a 1.8 Kb DNA region which is obtainable by the method according to the invention from the *Sorangium cellulosum* genome and which comprises the nucleotide part-sequence depicted in SEQ ID NO 1, as well as all other DNA sequences which are in the vicinity of this sequence and which, because of homologies which are present, can be regarded as structural or functional equivalents and therefore are able to hybridize with this sequence.

A DNA fragment which is likewise particularly preferred is one which comprises a 6.5 Kb DNA region which is obtainable by the method according to the invention from the *Sorangium cellulosum* genome and has the restriction pattern depicted in FIG. 1 and additionally also includes the 1.8 Kb region characterized in detail above.

A DNA fragment which exclusively comprises genomic DNA is very particularly preferred.

Likewise embraced by the present invention are DNA fragments which comprise sequence portions which have homologies with the nucleotide part-sequence, depicted in SEQ ID NO 1, of the 1.8 Kb region which is obtainable by the method according to the invention from the *Sorangium cellulosum* genome, which therefore can be found by use of this region or of parts thereof as hybridization probes within a genomic gene bank.

Preferred DNA fragments are likewise those which comprise sequence portions which have homologies with the 4.6 Kb BamHI fragment from the graI region of the granaticin gene cluster [ORF 1–4] of *Streptomyces violaceoruber* T ü22 and which therefore can be found by use of this 4.6 Kb fragment or of parts of this fragment as hybridization probe within a genomic gene bank of a soraphen-producing organism.

Another aspect of the present invention relates to the use of a DNA fragment which comprises a portion of a gene cluster which is responsible for soraphen biosynthesis, such as, for example, of one of the genes which is involved directly or indirectly in the biosynthesis, or parts thereof, as probe for finding adjacent overlapping DNA regions which can then in their turn again be used as probe for finding adjacent regions, which finally leads to complete identification of the gene cluster which flanks the start or initial region and is responsible for soraphen biosynthesis.

The present invention further relates to the DNA regions which can be obtained in the way described previously and which, if required, can be ligated together to give a single fragment which then comprises all those genes and other DNA sequences which flank within the Sorangium genome the firstly identified initial region in the form of a gene cluster and which in their totality are responsible for soraphen biosynthesis.

A preferred probe molecule is a DNA fragment which comprises a 1.8 Kb DNA region which can be obtained by the process according to the invention from the *Sorangium cellulosum* genome and which comprises the nucleotide part-sequence depicted in SEQ ID NO 1, but especially selected parts thereof. Particularly preferred sequence sections are those which can be obtained from the flanking regions located on the right and left, respectively, of the said 1.8 Kb region.

Likewise preferred for use as a probe molecule is a 6.5 Kb fragment which comprises a 6.5 Kb DNA region which can be obtained by the process according to the invention from the *Sorangium cellulosum* genome and which has the restriction pattern depicted in FIG. 1 and additionally includes the 1.8 Kb region characterized in detail above, but especially selected parts thereof. Particularly preferred sequence sections are those which can be obtained from the flanking regions located on the right and left, respectively, of the 1.8 Kb region.

The present invention additionally relates to recombinant DNA molecules which comprise one of the DNA fragments according to the invention, and to the plasmids and vectors derived therefrom. Likewise embraced are host organisms which are transformed with said plasmid DNA or vector DNA, including plant hosts.

The invention further relates to a method for the identification, isolation and cloning of a DNA fragment which comprises a DNA region which can preferably be obtained from the gene cluster, which is responsible for soraphen biosynthesis, within the genome of *S. cellulosum* and comprises at least one gene or a part of a gene or another DNA sequence which is involved directly or indirectly in the biosynthesis of soraphen, and which method essentially comprises the following measures:

(a) construction of a representative gene library of a soraphen-producing organism from the group of myxobacteria, which essentially comprises the totality of the bacterial genome distributed on single clones;

(b) screening of said clones using a specific DNA probe which hybridizes at least with a part of the gene cluster responsible for soraphen biosynthesis;

(c) selection of those clones which exhibit a hybridization signal with the DNA probe; and (d) isolation of a DNA fragment from said clone, which comprises a DNA region which comprises at least one gene or a pan of a gene or another DNA sequence which is involved directly or indirectly in the biosynthesis of soraphen.

The present invention further relates to a method for the identification and isolation of all those DNA sequences which are involved in the construction of the 'soraphen gene cluster' flanking the initial or start region, which comprises (a) constructing a representative gene library of a soraphen-producing organism from the group of myxobacteria, which essentially comprises the totality of the bacterial genome distributed on single clones;

(b) hybridizing said clones using one of the previously isolated DNA fragments or selected parts thereof as probe molecules, which overlap at least with a part of the adjacent DNA regions located on the right and left, respectively, within the 'soraphen gene cluster';

(c) selecting those clones which exhibit a strong hybridization signal with the DNA probe;

(d) isolating those fragments which comprise overlapping DNA regions from the clones selected according to (c), and isolating the fragment which projects furthest beyond the region of overlap;

(e) testing the DNA fragment isolated according to (d) for its ability to function within the 'soraphen gene cluster';

(f) if it is possible to detect a function of the DNA fragment isolated according to (d) within the scope of sorapben biosynthesis, repeating the method according to steps (a) to (e), wherein the DNA fragment isolated according to (d), or selected parts thereof, but especially those from the left or right flanking region of said fragment, function as DNA probes, until a function in soraphen biosynthesis is no longer detectable within the scope of the function test on the particular newly isolated DNA fragment, and thus the end of the gene cluster is reached; and (g) carrying out the method according to steps (a) to (f) where appropriate in the other direction which has not previously been selected.

DETAILED DESCRIPTION OF THE INVENTION

Figure 1:
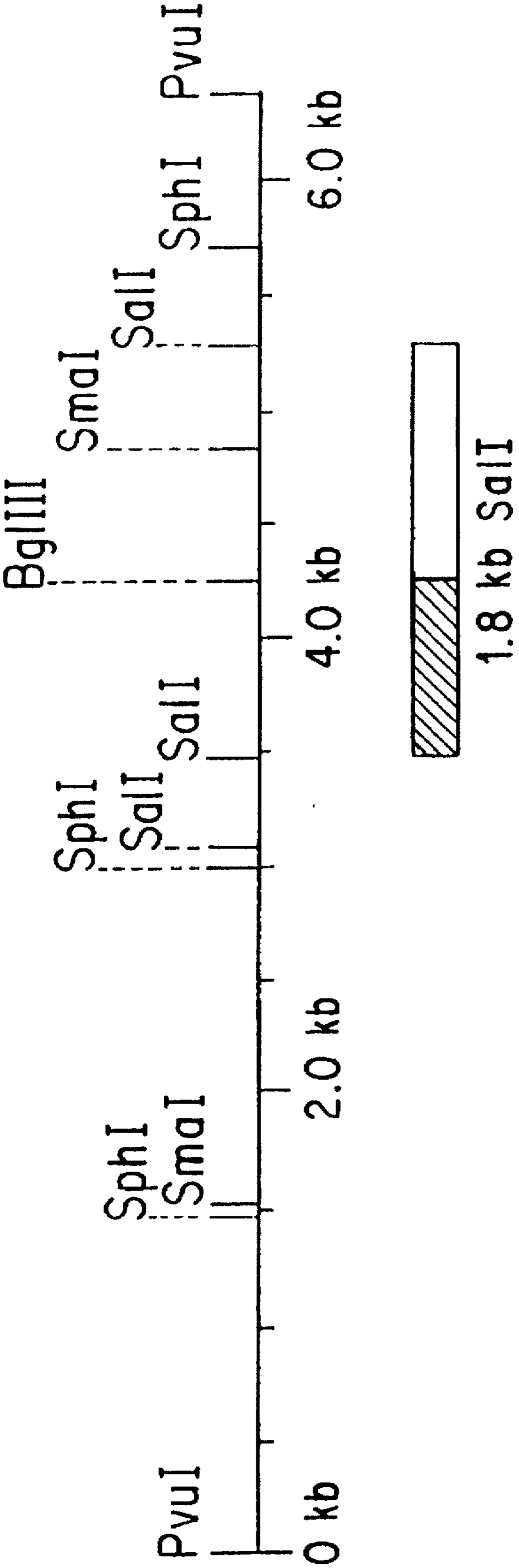

In order to facilitate interpretation and understanding of what is intended to be regarded as encompassed according to the application within the scope of the present invention, some of the terms essential for establishing the scope of protection are defined in detail hereinafter, that is to say a detailed explanation is given of the meaning they are intended to have within the scope of this invention:

DNA fragment: A piece of DNA which may comprise both coding and non-coding sections and which either can be obtained directly from a natural source or else can be prepared with the aid of recombinant or synthetic techniques or else a combination of said techniques.

Coding DNA sequence: A DNA sequence which is composed of individual nucleotide constituents in accordance with the rules of the genetic code and which comprises structural information and which, after transcription and translation have taken place, results in the production of a corresponding polypeptide.

Gene: A defined region which is located within a genome and which, besides the abovementioned coding DNA sequence, comprises other, primarily regulatory, DNA sequences which are responsible for the control of the expression, that is to say the transcription and translation, of the coding portion.

Essentially homologous: This ten relates primarily to DNA and amino-acid sequences which must, because of the homologies present, be regarded as structural and/or functional equivalents. The structural and/or functional differences between the relevant sequences, which should as a rule be minimal, can have very different causes. Thus, for example, these may comprise mutations which occur naturally or else are induced artificially, or else the differences to be observed compared with the initial sequence are based on a specific modification which can be introduced, for example, within the scope of a chemical synthesis.

Functional differences can be regarded as minimal when, for example, the nucleotide sequence coding for a polypeptide, or a protein sequence, has essentially the same characteristic properties as the initial sequence, within the area of enzymatic activity, of immunological reactivity or, in the case of a nucleotide sequence, of gene regulation.

Structural differences can be regarded as minimal as long there is a significant overlap or similarity between the different sequences, or the latter have at least similar physical properties. The latter include, for example, the electrophoretic mobility, chromatographic similarities, sedimentation coefficients, spectrophotometric properties, etc. In the case of the nucleotide sequences, the agreement should be at least 60%, but preferably 75% and, very particularly preferably, 90% and more. In the case of the amino-acid sequence, the corresponding values are at least 70%, but preferably 80% and, particularly preferably, 90%. A 99% agreement is very particularly preferred.

Gene(s) or DNA of heterologous origin: A DNA sequence which codes for a specific product or products or fulfills a biological function and which originates from a different species than that into which the gene is inserted; said DNA sequence is also called foreign gene or foreign DNA or exogenous DNA.

Gene(s) or DNA of homologous origin: A DNA sequence which codes for a specific product or products or fulfills a biological function and which originates from the same species into which the gene is inserted. This DNA is also called exogenous DNA.

DNA homology: Degree of agreement between two or more DNA sequences.

Synthetic gene(s) or DNA: A DNA sequence which codes for a specific product or products or fulfills a biological function and which is prepared by a synthetic route.

Promoter: A DNA expression control sequence which ensures the transcription of any desired homologous or heterologous DNA gene sequence in a host cell as long as said gene sequence is linked in an operable manner to a promoter of this type and the latter is active in said host cell.

Termination sequence: DNA sequence at the end of a transcription unit which signals the end of the transcription process.

Overproducing promoter (OPP): Promoter which is able in a host cell to bring about the expression of any functional gene sequence(s) linked in an operable manner to an extent (measured in the form of the RNA or of the amount of polypeptide) which is distinctly higher than is naturally observed in host cells not transformed with said OPP.

3'/5' non-translated region: DNA sections which are located downstream/upstream of the coding region and which, although transcribed into mRNA, are not translated into a polypeptide. This region comprises regulatory sequences such as, for example, the ribosome binding site (5').

DNA expression vector: Cloning vehicle, such as, for example, a plasmid or a bacteriophage, which comprises all signal sequences which are necessary for expression of an inserted DNA in a suitable host cell.

DNA transfer vector: Transfer vehicle, such as, for example, a plasmid or a bacteriophage vector, which makes it possible to insert genetic material into a suitable host cell.

Homologous recombination: Reciprocal exchange of DNA fragments between homologous DNA molecules.

Mutants, variants: Derivative, produced spontaneously or else artificially using known process measures such as, for example, UV treatment, treatment with mutagenic agents etc., of a microorganism, which still has the features and properties, essential to the invention, of the initial strain which this has received because of the transformation with exogenous DNA.

To isolate the DNA fragments according to the invention, initially genomic gene banks are set up from the interesting organism strains which synthesize a required secondary metabolite, but especially soraphen.

Genomic DNA can be obtained in various ways from a host organism, for example by extraction from the nuclear fraction and purification of the extracted DNA with the aid of known methods.

The fragmentation, which is necessary for setting up a representative gene bank, of the genomic DNA which is to be cloned to a size suitable for inserting into a cloning vector can take place either by mechanical shearing or else preferably by cutting with suitable restriction enzymes. Particularly preferred in this connection within the scope of this invention is a partial cleavage of the genomic DNA, which leads to mutually overlapping DNA fragments.

Suitable cloning vectors which are already used routinely for producing genomic and/or cDNA gene libraries comprise, for example, phage vectors such as the λ charon phages or else bacterial vectors such as the *E. coli* plasmid pBR322. Other suitable cloning vectors are known to the person skilled in the art.

Particularly suitable for setting up genomic gene banks are so-called cosmid vectors which comprise both portions from the DNA of plasmids and the constituents, which are essential for packaging, from the genome of lambda phages, the so-called 'cos' sites. The cosmids acquire, via the plasmid portion, gene sequences which code for one or more markers which are required within the scope of selection, as well as the DNA regions which are essential for autonomous replication in a bacterial host. Cosmids are, as a rule, very small molecules, which provides them with the capacity for cloning correspondingly large DNA fragments. This makes them particularly suitable for use within the scope of the present invention.

Likewise suitable for setting up genomic gene banks are vector variants derived from cosmids, such as, for example, the charomids, which comprise a variable amount of 'full DNA' and therefore are able to compensate for any differences in size with the DNA to be cloned.

Suitable clones which comprise the required genes or gene fragments can then be discovered from the gene libraries set up in this way within the scope of a screening programme, for example with the aid of suitable probe molecules [DNA probes] and subsequently isolated. Various methods are available for discovering suitable clones, such as, for example, differential colony hybridization or plaque hybridization. When expression gene banks are used it is additionally possible to employ immunological detection methods which are based on identification of the specific translation products.

It is possible to use as a probe molecule, for example, a DNA fragment which has already been isolated previously from the same or else a structurally related gene which, because of the homologies present, is able to hybridize with the corresponding sequence section within the required gene or gene cluster which is to be identified. Preferred for use as probe molecule within the scope of the present invention is a DNA fragment which can be obtained from a gene or another DNA sequence which plays a part in the synthesis of a known polyketide antibiotic. A particularly preferred probe molecule is a 4.6 Kb BamHI fragment from the graI region of the granaticin gene cluster [ORF 1–4] of *Streptomyces violaceoruber* Tü22 [Sherman D. et al, 1989].

In place of the probe from the graI region of *Streptomyces violaceoruber* Tü22, which is used for finding a starting point within the 'soraphen gene cluster' and which exhibits only a relative weak hybridization signal, it is now also possible, of course, to use parts of the fragments isolated within the scope of the present invention, such as, for example, of the 1.8 Kb SalI fragment, as probe molecules, which, because of the homologies present, also leads to unambiguous results with other soraphen-producing Sorangium strains.

Once the amino-acid sequence of the gene to be isolated, or else at least parts of this sequence, are known it is possible in an alternative embodiment to design an appropriate corresponding DNA sequence on the basis of this sequence information. Since, as is known, the genetic code is degenerate, it is possible in the majority of cases to use different codons for one and the same amino acid. The result of this is that, apart from a few exceptional cases, as a rule a particular amino-acid sequence can be encoded by a whole series of mutually similar oligonucleotides. However, it should be noted in this connection that only one member of this series of oligonucleotides actually agrees with the corresponding sequence within the gene which is sought. In order to limit the number of possible oligonucleotides from the outset, it is possible, for example, to have recourse to the rules established by Bibb M. et al (1984) for the use of codons, which take account of the frequency with which a particular codon is used in prokaryotic cells with high guanine and cytosine content.

It is thus possible on the basis of this information to design oligonucleotide molecules which can be used as probe molecules for identifying and isolating suitable clones, by hybridizing said probe molecules with genomic DNA in one of the previously described methods.

In order to facilitate the detectability of the required gene or else parts of a required gene it is possible to label one of the previously described DNA probe molecules with a suitable, easily detectable group. A detectable group is intended to mean within the scope of this invention every material which has a particular, easily identifiable, physical or chemical property.

Materials of this type are already widely used, especially in the area of immunoassays, and in the majority of cases can also be used in the present application. Particular mention may be made at this point of enzymatically active groups such as, for example, enzymes, enzyme substrates, coenzymes and enzyme inhibitors, furthermore fluorescent and luminescent agents, chromophores and radioisotopes such as, for example, $^{3}H$, $^{35}S$, $^{32}P$, $^{125}I$ and $^{14}C$. The easy detectability of these markers is based, on the one hand, on their intrinsically present physical properties (for example fluorescence markers, chromophores, radioisotopes) and, on the other hand, on their reaction and binding properties (for example enzymes, substrates, coenzymes, inhibitors).

General methods relating to DNA hybridization are described, for example, by Maniatis T et al (1982) and by Haymes B. T. et al (1985).

Those clones within the previously described gene libraries which are able to hybridize with a probe molecule and which can be identified with the aid of one of the above-mentioned detection methods can then be further analyzed in order to determine the extent and nature of the coding sequence in detail.

An alternative method for identifying cloned genes is based on the construction of a gene library which is constructed from expression vectors. This entails, in analogy to the methods already described previously, genomic DNA which is able to express a required gene product being initially isolated and subsequently cloned into a suitable expression vector. The gene libraries produced in this way can then be screened with the aid of suitable measures such as, for example, using complementation studies, and those clones which comprise the required gene or else at least a part of this gene as insert can be selected.

It is thus possible, with the aid of the previously described methods, to isolate a gene which codes for a particular gene product.

For further characterization, the DNA sequences purified and isolated in the manner previously described are subjected to a restriction analysis and to a sequence analysis.

The isolated fragments are characterized within the scope of the restriction analysis on the basis of their restriction cleavage sites, by being completed digested with suitable restriction enzymes such as, for example, BglII, SphI and SmaI. Said restriction enzymes can in this connection be employed either singly or else in combination with one another. The size of the resulting fragments can be determined after fractionation on an agarose gel by comparison with a size standard.

For the sequence analysis, the previously isolated DNA fragments are initially decomposed with the aid of suitable restriction enzymes into fragments and subsequently cloned into suitable cloning vectors such as, for example, the M13 vectors mp18 and mp19. The sequencing is carried out, as a rule, in the 5'→3' direction, preferably using the dideoxynucleotide chain-termination method of Sanger [Sanger et al, 1977] or the Maxam and Gilbert method [Maxam and Gilbert, 1980]. In order to avoid errors in the sequencing, it is advantageous to sequence the two DNA strands in parallel. Standardized sequencing kits which help to reduce the experimental effort and whose use is therefore preferred within the scope of this invention are now obtainable. The analysis of the nucleotide sequence and of the corresponding amino-acid sequence is preferably carried out with computer assistance using suitable, commercially obtainable computer software [for example GCG software from the University of Wisconsin].

Various alternatives are available for analysis of the cloned DNA fragment with respect to its function within the scope of soraphen biosynthesis.

Thus, for example, there is the possibility within the scope of complementation experiments with defective mutants not only of establishing the involvement in principle of a gene or gene fragment in secondary metabolite biosynthesis but, in addition, of verifying specifically the synthetic step in which said DNA fragment is involved.

In an alternative form of analysis, the demonstration takes place in exactly the opposite sense. Transfer of plasmids which comprise DNA sections which have homologies with corresponding sections of the myxobacterial genome results in integration of said homologous DNA sections into the chromosomal DNA of the myxobacteria at the site of the homology via homologous recombination. If the homologous DNA section is, as in the present case, a region within an intact gene cluster, the plasmid integration results in inactivation of this cluster by so-called gene disruption and consequently in a suspension in secondary metabolite production.

The bases for carrying out the detection method described above are described in EP-A No. 92810128.6 and Jaoua et al (1992). It was possible to show there for the first time that it is possible for foreign DNA of homologous or heterologous origin or a combination of genetic material of homologous and heterologous origin to be inserted into the myxobacterial cell and there integrated, via homologous recombination, specifically at a site, which is accurately defined on the basis of the homologies present, into the chromosome of said myxobacteria as long as the latter have sufficient homologies with corresponding sections within the genome.

According to the present state of knowledge, it is assumed that a homologous region which comprises at least 100 Bp, but preferably more than 1000 Bp, is sufficient to bring about the required recombination event.

However, a homologous region which extends over a range from 0.3 to 4 Kb, but in particular over a range from 1 to 3 Kb, is preferred.

Preferably provided for the preparation of suitable plasmids which have a homology with the myxobacterial chromosome which is sufficient for integration via homologous recombination is a subcloning step in which the previously isolated cosmid DNA is digested and fragments of suitable size are isolated and subsequently cloned into a suitable plasmid.

The ligation of homologous DNA fragments and of DNA fragments of homologous and heterologous origin into a suitable cloning vector takes place with the aid of standard methods as are described, for example, by Maniatis et al, 1982.

As a rule, this entails the vector and the DNA to be integrated initially being cut with suitable restriction enzymes. Examples of suitable restriction enzymes are those which provide fragments with blunt ends, such as, for example, SmaI, HpaI and EcoRV, or else enzymes which form cohesive ends, such as, for example, EcoRI, SacI, BamHI, SalI, PvuI, etc.

Both fragments with blunt ends and those with cohesive ends which are complementary to one another can be linked again, with the aid of suitable DNA ligases, to give a single continuous DNA molecule.

Blunt ends can also be produced by treatment of DNA fragments which have protruding cohesive ends with the Klenow fragment of *E. coli* DNA polymerase by filling in the gaps with the appropriate complementary nucleotides.

On the other hand, cohesive ends can also be produced artificially, for example by attaching complementary homopolymer tails to the ends of a required DNA sequence and of the cut vector molecule using a terminal deoxynucleotidyl-transferase or else by attaching synthetic oligonucleotide sequences (linkers) which have a restriction cleavage site and subsequently cutting with the appropriate enzyme.

It is possible in principle to use for the preparation and replication of the previously described constructs all conventional cloning vectors such as, for example, plasmid vectors or bacteriophage vectors as long as they have replication and control sequences which originate from species which are compatible with the host cell.

As a rule, the cloning vector has an origin of replication, in addition specific genes which lead to phenotypical selection features in the transformed host cell, in particular to resistances to antibiotics. The transformed vectors can be selected on the basis of these phenotypical markers after transformation into a host cell.

Selectable phenotypical markers which can be used within the scope of this invention comprise, for example, without this representing a limitation on the subject-matter of the invention, resistances to ampicillin, tetracycline, chloramphenicol, hygromycin, G418, kanamycin, neomycin and bleomycin. A prototrophy for particular amino acids can, for example, function as further selectable marker.

Primarily preferred within the scope of the present invention are *E. coli* plasmids such as, for example, the plasmid pSUP2021 used within the scope of the present invention.

Primarily suitable as host cells for the previously described cloning within the scope of this invention are prokaryotes, including bacterial hosts such as, for example, *A. tumefaciens, E. coli, S. typhimurium* and *Serratia marcescens*, furthermore pseudomonads, actinomycetes, salmonellae and myxobacteria themselves.

*E. coli* hosts are particularly preferred, such as, for example the *E. coli* HB101 strain.

Competent cells of the *E. coli* HB101 strain are moreover produced with the aid of the methods customarily used for transformation of *E. coli* [see: "General recombinant DNA techniques"].

The colonies resulting after transformation and subsequent incubation on a suitable medium are subjected to a differential screening by plating out on selective media. It is then possible subsequently to isolate the appropriate plasmid DNA from those colonies which comprise plasmids with DNA fragments cloned in.

Recombinant plasmids of various sizes are obtained in this way. It is then possible after restriction analysis for plasmids of suitable size to be selected for the subsequent insertion of the plasmid DNA into the myxobacterial cell. This DNA transfer can moreover take place either directly or else via an intermediate host (donor cell) within the scope of a conjugal transfer.

Conjugal transfer from a donor cell to the myxobacterial recipient is preferred within the scope of this invention.

The DNA to be transferred within the scope of this conjugal transfer can moreover be either initially cloned, as previously described, in one of the customarily used cloning vectors and subsequently transformed into a suitable intermediate host which functions as donor cell. However, the circuitous route via the intermediate host can be avoided by using a host strain which is suitable both for cloning of DNA and for use as donor cell within the scope of the conjugation.

Intermediate hosts which can be used as donor cells within the scope of this invention are essentially prokaryotic cells selected from the group consisting of *E. coli*, pseudomonads, actinomycetes, salmonellae and myxobacteria themselves.

The precondition for conjugal transfer of plasmid DNA from a donor cell to a recipient is the presence of transfer (tra) and mobilization functions (mob). In this connection, the mobilization function must comprise at least the origin of transfer (oriT) and be located on the plasmid to be transferred. By contrast, the transfer function (tra) can be located either on the plasmid or on a helper plasmid or else be present integrated into the chromosome of the donor cell.

Plasmids which meet the abovementioned precondition and are therefore preferred within the scope of this invention essentially belong to incompatibility groups P, Q, T, N, W and ColI. The prototype of the P group plasmids is the plasmid RP4. Particularly preferred within the scope of this invention is the plasmid pSUP2021 which comprises a 1.9 Kb fragment from the plasmid RP4 which has as constituent of the mob function (RP4mob) the origin of transfer (oriT). Other plasmids with the mob function (RP4mob) such as, for example, pSUP101, pSUP301, pSUP401, pSUP201, pSUP202, pSUP203 or pSUP205, and the derivatives derived therefrom [Simon et al (1988)], can likewise be used within the scope of the method according to the invention.

It has proven advantageous to expose the myxobacterial recipient during the course of the conjugal transfer to a brief heat treatment before incubation with the donor strain. The recipient cells are preferably preincubated at a temperature of 35° C. to 60° C., preferably at a temperature of 42° C. to 55° C. and very particularly preferably at a temperature of 48° C. to 52° C., for one to 120 minutes, but especially for 5 to 20 minutes.

Used in a preferred embodiment of the present invention is a *E. coli* donor strain which comprises the transfer genes (tra) of plasmid RP4 incorporated in the chromosomal DNA. The *E. coli* donor strain W3101 (pME305) which comprises the helper plasmid pME305 which possesses the transfer function (tra) of RP4 is particularly preferred within the scope of this invention.

Of particular interest for methodological techniques and therefore very particularly preferred within the scope of this invention are bacterial strains which are suitable both as hosts for the cloning of vectors with integrated DNA sequences and for use as donor cell within the scope of the conjugal transfer. Likewise particularly preferred are bacterial strains which are restriction negative and thus do not degrade inserted foreign DNA. Both of the abovementioned criteria are met in an ideal manner by the *E. coli* strain ED8767 (pUZ8) which is, however, mentioned at this point only as representative of other suitable bacterial strains and is not intended to limit the application in any way.

Besides the previously described conjugal gene transfer from a donor cell into a myxobacterial recipient, it is also, of course, possible to use other suitable gene transfer methods for inserting genetic material into myxobacteria. Mention may be made here primarily of gene transfer via electroporation, within the scope of which the myxobacterial cells are briefly exposed to high electric field strengths [Kuspa and Kaiser (1989)]. The general outline conditions for electroporation of prokaryotic cells are described in detail in U.S. Pat. No. 4,910,140.

The DNA fragment according to the invention, which comprises a DNA region which is involved directly or indirectly in the biosynthesis of soraphen and which can be obtained in the previously described way from the gene cluster of soraphen biosynthesis can also be used as starting clone for the identification and isolation of other DNA regions which are adjacent and overlap with the latter from said gene cluster.

This can be achieved, for example, by carrying out a so-called chromosome walking, using the previously isolated DNA fragment or else in particular its 5'-and 3'-located flanking sequences, within a gene library composed of DNA fragments with mutually overlapping DNA regions. The procedure within the scope of chromosome walking are known to the person skilled in this art. Details can be obtained, for example, from the publications by Smith C. L. et al (1987) and Wahl G. L. et al (1987).

The precondition for chromosome walking is the presence of clones with coherent and mutually overlapping DNA fragments of maximum length within a gene library, and of a suitable starting clone which comprises a fragment which is located in the vicinity of or else preferably within the region to be analyzed. If the exact location of the starting clone is unknown, the walking is preferably carried out in both directions as well.

The actual walking step starts by using the starting clone, once it has been identified and isolated, as a probe in one of the previously described hybridization reactions in order to detect adjacent clones which have regions overlapping with the starting clone. It is moreover possible by hybridization analysis to identify the fragment which projects furthest beyond the overlapping region. This fragment is then used as the initial clone for the second walking step, and in this case the fragment which overlaps with said second clone in the same direction is identified. In this way, by continuous advance along the chromosome, a collection of overlapping DNA clones which cover a large DNA range is obtained. These can then, where appropriate after one or else several subcloning steps have been carried out, be ligated together with the aid of known methods to give a fragment which comprises parts or else, preferably, all constituents essential for soraphen biosynthesis.

In place of the very large and unwieldy complete fragment, preferably used for the hybridization reaction to identify clones with overlapping flanking regions is a partial fragment which is from the left or right flanking region and which can be obtained by a subcloning step. Because of the smaller size of said partial fragment, the hybridization reaction results in fewer positive hybridization signals so that the analytical effort is distinctly less than when the complete fragment is used. It is additionally advisable to characterize the partial fragment in detail in order to exclude the presence of relatively large portions of repetitive sequences, which may be scattered over the entire genome and thus would greatly impede a targeted sequence of walking steps.

Since the gene cluster responsible for soraphen biosynthesis covers a very large genome region, it is advantageous within the scope of the present invention to carry out a so-called large-step walking or cosmid walking. It is possible in these cases, by using cosmid vectors which permit the cloning of very large DNA fragments, to cover a very large DNA region, which can comprise up to 45 Kb, with a single walking step.

In a specific embodiment of the present invention, to construct a cosmid gene bank of *S. cellulosum* complete DNA in a size of the order of 100 Kb is isolated and subsequently digested with the aid of suitable restriction endonucleases.

Preferred in this connection is a 3-fold partial digestion with Sau3A, with the individual digestions being carried out independently of one another in order thus to achieve a restriction level with maximum differences.

The digested DNA is subsequently extracted in the customary way, in order to remove the endonuclease which is still present, and is precipitated and finally concentrated. The resulting fragment concentrate is then fractionated, for example via a density gradient centrifugation, according to the size of the individual fragments. Fractions obtainable in this way can, after dialysis, be analyzed on an agarose gel. The fractions which comprise fragments of suitable size are pooled and concentrated for further processing. Regarded as particularly suitable within the scope of its invention are fragments with a size of the order of 30 Kb to 45 Kb, but preferably from 40 Kb to 45 Kb.

In parallel with the fragmentation described above, or later, a suitable cosmid vector such as, for example, pHC79 [Hohn and Collins, 1980] is completely digested with a suitable restriction enzyme such as, for example, BamHI for the subsequent ligase reaction.

The ligation of the cosmid DNA to the *S. cellulosum* fragments which have been fractionated according to their size can be carried out using a $T_4$DNA ligase. The ligation mixture obtainable in this way is, after a sufficient incubation time, packaged into λ phages, using, for reasons of economy of the method, preferably one of the commercial packaging kits which can now be obtained from various suppliers such as, for example, from STRATAGEN or PROMEGA.

The resulting phage particles are then used to infect a suitable host strain. A $recA^-$ *E. coli* strain such as, for example, *E. coli* HB 101 is preferred. The selection of transfected clones and the isolation of the plasmid DNA can be carried out by means of generally known methods.

The screening of the gene bank for DNA fragments which play a part in soraphen biosynthesis is carried out with the aid of a specific hybridization probe which is assumed to comprise DNA regions which have sufficient homologies with corresponding regions within the 'soraphen gene cluster'.

The starting material which can be used for preparing said hybridization probe is the plasmid pIJ5200 [Sherman et al, 1989] which comprises a 4.6 Kb BamHI fragment of the graI region [granaticin gene cluster ORF 1–4] of *Streptomyces violaceoruber* Tü22 cloned into the BamHI cleavage site of pUC 18.

In order to remove interfering DNA sequences which originate from the plasmid vectors and which might have adverse effects on the gene bank analysis from the 4.6 Kb, said fragment is preferably cloned into a Streptomyces vector and the latter is transformed into a competent Streptomyces strain.

After selection and restriction analysis, suitable clones which comprise the 4.6 Kb fragment cloned into the plasmid DNA are selected and cultivated for plasmid isolation. The plasmid DNA is isolated with the aid of known methods such as, for example, the CsCl gradient method, and the 4.6 Kb fragment is removed after complete digestion of the plasmid DNA with BamHI.

The 4.6 Kb fragment isolated in this way is radioactively labelled by carrying out a nick translation using d-$CTP^{32}$. It is advisable in this case too, for reasons of economy of the method, to use a commercial nick translation kit which is marketed, for example, by Bethesda Research Laboratories Life Technologies Inc.

It is now, of course, also possible to use as a probe molecule in place of the probe which was used for finding a starting point within the 'soraphen gene cluster' and which was obtained from the graI region of *Streptomyces violaceoruber* Tü22, and which reveals only a relatively weak hybridization signal, parts of the fragments isolated within the scope of the present invention, such as, for example, a 1.8 Kb SalI fragment, which leads, because of the homologies present, to unambiguous results with other soraphen-producing Sorangium strains too.

The screening of the gene bank with the aid of the radioactively labelled probe preferably takes place within the scope of a hybridization analysis. The latter can be carried out, for example, in the form of a colony hybridization which is described, for example, by Maniatis et al [page 326–328; (1982)].

The clones which show the strongest hybridization signals are selected and incubated on a suitable medium [for example LB medium] and then used to isolate the plasmid DNA [as described by Maniatis et al (1982); pages 368 and 369].

The isolated plasmids are then digested with a suitable restriction enzyme such as, for example, SalI, and the fragments obtained in this way are fractionated on an agarose gel. The resulting fragments are then subjected to a Southern hybridization which can be carried out within the scope of a Southern capillary blotting. A cosmid clone [p98/1] which shows a strong band at 1.8 Kb in the audioradiograph is selected for subsequent work. This cosmid clone is first cultivated in a suitable medium for amplification of the plasmid DNA. After the plasmid DNA has been isolated it is completely digested with a suitable restriction enzyme [for example SalI] and the fragments obtainable in this way are fractionated by electrophoresis on an agarose gel. The required 1.8 Kb DNA fragment can then be removed from the agarose gel by electroelution.

The 1.8 Kb fragment obtainable in this way is subsequently cloned into a bacterial plasmid in a ligase reaction. The *E. coli* plasmid pBR322 is preferred within the scope of this invention.

The resulting ligated DNA is subsequently cloned into cells, which have been made competent, of a $recA^-$ strain of *E. coli*, but preferably into cells of the *E. coli* strain HB101 Maniatis et al, 1982; pages 250 and 25 1 ) and transferred to a selective medium.

Suitable colonies can be found by differential screening of the resulting transformed colonies, and their plasmid DNA can be isolated [as described by Maniatis et al, 1982; pages 368 and 369]. The isolated plasmid DNA is then cut with a suitable restriction enzyme such as, for example, SalI, and analyzed by agarose gel electrophoresis for the size of its inserted fragments, preferably employing as a comparison standard the previously selected cosmid [p98/1].

A plasmid [p108/III2] which comprises an additional fragment of the required size can then be isolated from the gel in the manner previously described. The identity of this additional fragment to the 1.8 Kb fragment of the previously selected cosmid [p98/1] can then be confirmed by Southern transfer and hybridization with the 4.6 Kb DNA probe from *S. violaceoruber.*

The function analysis of the previously isolated 1.8 Kb DNA fragment can be carried out within the scope of a gene disruption experiment.

This entails initially the cosmid DNA [p98/1] being completely digested with the aid of a suitable restriction enzyme, and the resulting fragments being fractionated, e.g. when using PvuI, fragments with sizes of about 10, 6.5, 4.2 and 4 Kb can be obtained. Fragments of the required size can then be cloned into a suitable vector which comprises the functions required for conjugal transfer. The plasmid pSUP2021 which comprises a fragment from the plasmid RP4, which has a mob function (RP4mob) and as constituent of this mob function an origin of transfer (oriT), is preferred. After transformation of host cells which have been made competent,—which are preferably cells of the *E. coli* strain HB101—, it is then possible very simply to identify and select positive clones, that is to say clones whose plasmid DNA comprises fragments of the required size.

The plasmids obtainable in this way can then be used for conjugal transfer into *S. cellulosum.* The donor strain which can preferably be used for this is an *E. coli* strain which comprises the transfer genes (tra) of plasmid RP4 incorporated into the chromosomal DNA. Preferred within the scope of this invention is the *E. coli* donor strain W3101 (pME305) which comprises the helper plasmid pME305 which possesses the transfer function (tra) of RP4.

Of particular interest for methodological techniques and therefore very particularly preferred within the scope of this invention are bacterial strains which are suitable both as hosts for the cloning of vectors with integrated DNA sequences and for use as donor cells within the scope of the conjugal transfer. Likewise particularly preferred are bacterial strains which are restriction negative and thus do not degrade inserted foreign DNA. Both of the previously mentioned criteria are fulfilled in an ideal manner by the *E. coli* strain ED8767(pUZ8) whose use is therefore particularly preferred within the scope of this invention.

When the helper plasmid pUZ8, which has no ampicillin-resistance gene, is used it is possible to dispense with the cloning step in the *E. coli* intermediate host HB101 because direct cloning in the *E. coli* donor strain ED8767 which is intended for the conjugal transfer is now possible.

The plasmid pUZ8 is a derivative of the plasmid RP4 which embraces a wide host range and is described by Datta et al (1971). The modifications compared with the initial plasmid RP4 essentially relate to the ampicillin-resistance gene and to the insertion element IS21, both of which are deleted, and to the incorporation of an additional gene which confers resistance to mercury ions [see Jaoua et al (1987)].

The plasmid DNA can therefore now be directly transformed into the *E. coli* strain ED8767. For this, competent cells of the *E. coli* strain ED8767 are prepared with the aid of the methods customarily used for the transformation of *E. coli* [see: "General recombinant DNA techniques"].

The colonies resulting after transformation and subsequent incubation on a suitable selective medium are subjected to a differential screening by parallel plating out on ampicillin-containing [60 μg/ml] and ampicillin-free medium. It is subsequently possible to isolate those colonies which have lost their ampicillin resistance owing to the integration of the Sorangium DNA fragments. The cultures obtainable in this way can then be employed directly as donor cells for the conjugative transfer of the recombinant plasmids into *Sorangium cellulosum* cells.

For the actual transfer, *Sorangium cellulosum* cells in the stationary phase are mixed with a late log phase culture of *E. coli* donor cells which comprise a comparable proportion of cells.

It proves advantageous in this case to expose the Sorangium recipient cells to a brief heat treatment in a water bath before the conjugation with *E. coli*. The best transfer results with the *Sorangium cellulosum* strain SJ3 can be achieved with a heat treatment at a temperature of 50° C. for 10 minutes. Transfer frequencies of $1–5\times10^{-5}$ can be achieved under these conditions, which corresponds to an increase by a factor of 10 compared with a method without previous heat treatment.

After various selection steps have been carried out it is possible to obtain transconjugants of *Sorangium cellulosum* which comprise the required plasmid DNA. The transformation frequency for the transfer of plasmid DNA to Sorangium averages $1–3\times10^{-6}$ based on the recipient strain.

Transfer of plasmids which comprise DNA sections which are homologous with corresponding sections within the *Sorangium cellulosum* genome leads to integration of said DNA sections into the chromosomal *Sorangium cellulosum* DNA at the site of the homology via homologous recombination. If the homologous region is a section within a gene cluster, for example that for soraphen biosynthesis, the plasmid integration results in inactivation of this cluster by so-called gene disruption. This method thus permits analysis of the function of a cloned DNA fragment in *Sorangium cellulosum*.

To examine the function of the PvuI fragments of cosmid p98/1, well-grown transconjugant colonies are transferred to and cultivated on a selective medium which contains kanamycin phleomycin and streptomycin as selective agents.

One or more intermediate cultivation steps are followed by transfer to a medium which contains an adsorbent such as, for example, a polymeric adsorber resin which binds the soraphen released by the bacteria.

After incubation for several days, the adsorbent is removed and the adherent soraphen is extracted, for example by shaking with a suitable solvent such as, for example, isopropanol. Quantitative soraphen analysis can then be carried out with the aid of an HPLC method, preferably using a UV detector at a wavelength of 210 nm.

For further characterization of the previously described 6.5 Kb fragment the latter is subjected to a restriction analysis, and subsequently the 1.8 Kb fragment comprised in said 6.5 Kb fragment is sequenced.

To characterize the 6.5 Kb PvuI fragment on the basis of restriction cleavage sites, said fragment is completely digested with suitable restriction enzymes such as, for example, BglII, SphI and SmaI, which are employed singly or in combination with one another. The size of the resulting fragments can be determined after fractionation on an agarose gel by comparison with a size standard.

Digestion of the 6.5 Kb PuvI fragment with BglII yields two fragments 4.3 Kb and 2.3 Kb in size, and that with SphI yields 4 fragments 2.8 Kb, 1.5 Kb, 0.7 Kb in size. Combination of the two enzymes [BglII and SphI] results in 5 fragments 1.6 Kb, 1.5 Kb, 1.5 Kb, 1.2 Kb, 0.7 Kb in size. Digestion with SmaI provides three fragments which have a size of 2.9 Kb, 2.0 Kb and 1.6 Kb.

In this case, because of the measurement method used, the actual size of the fragments may differ by ±10% from the stated value. The position of the BglII, SphI and SmaI cleavage sites on the 6.5 Kb fragment of cosmid p98/1 can be established on the basis of the fragment sizes found, as depicted in FIG. 1.

To prepare for the subsequent sequencing of the 1.8 Kb fragment comprised in the previously characterized 6.5 Kb fragment it is initially isolated from the plasmid [p108/III2] and subsequently cloned into a suitable vector.

The identity of the 1.8 Kb SalI fragment comprised in the 6.5 Kb PvuI fragment of clone pSN105/7 to the 1.8 Kb fragment cloned into the plasmid p108/1112 can be demonstrated on the basis of hybridization experiments.

Preferred within the scope of the present invention is an M13mp18 or an M13mp19 vector, each of which can be obtained commercially, for example from GIBCO-BRL (Basel, CH). The cloning into these vectors and the subsequent transfection of a suitable *E. coli* host can be carried out by the methods described by Maniatis et al (1989) [page 4.35–4.38].

The recombinant phage plaques (colorless) obtained in this way can be isolated as described by Maniatis et al [page 4.25; (1989)] and replicated in a suitable *E. coli* host. Analysis of the recombinant phages for an insert fragment of the correct size can likewise be carried out by means of known methods using gel electrophoresis [Maniatis et al [page 4.39–4.40; (1989)]. A larger amount of the single-stranded DNA from the phages with the required insert is then isolated [Maniatis et al [page 4.29–4.30; (1989)].

The DNA sequencing can preferably be carried out using a commercial sequencing kit. Preferred within the scope of this invention is the T7 sequencing kit from PHARMACIA, which operates by the dideoxy method of Sanger (1977). This entails employing the previously isolated single-stranded DNA as a template. All the sequencing operations are carried out in accordance with the instructions of the Pharmacia T7 sequencing kit (1991 instructions, No. xy-010-00-08) using the universal primer contained in the kit and the $^{35}S$ dATP which (Amersham) is used for the radioactive labeling. The samples obtainable in this way are subsequently fractionated by electrophoresis on a denaturing polyacrylamide gel (6%) and examined by autoradiography with an X-ray film [Kodak X-OmatS]. Details of the procedure can be found in the following examples and the instructions of Maniatis et al [page 13.45–13.58; (1989)].

It is possible on the basis of the DNA sequence information obtainable in this way to synthesize oligonucleotides which can then be employed as primers for sequencing the regions of the 1.8 Kb SalI fragments which are located further inside.

NON-LIMITING EXEMPLARY EMBODIMENTS

General recombinant DNA techniques

Since many of the recombinant DNA techniques used in this invention are routine for the person skilled in the art, a brief description of these generally used techniques is to be given hereinafter. All these methods are described in the Maniatis et al (1982) reference unless special reference is made thereto.

A. Cutting with restriction endonucleases

The reaction mixture typically contains about 50 to 500 µg/ml DNA in the buffer solution recommended by the manufacturer, primarily New England Biolabs, Beverly, Mass. and Böhringer, Mannheim (FRG). 2 to 5 units of restriction endonucleases are added for each µg of DNA, and the reaction mixture is incubated at the temperature recommended by the manufacturer for one to three hours. The reaction is stopped by heating at 65° C. for 10 minutes or by extraction with phenol, followed by precipitation of the DNA with ethanol. This technique is also described on pages 104 to 106 of the Maniatis et al (1982) reference.

B. Treatment of the DNA with polymerase in order to generate blunt ends 50 to 500 µg/ml DNA fragments are added to a reaction mixture in the buffer recommended by the manufacturer, primarily New England Biolabs, Beverly, Mass. and Böhringer, Mannheim (FRG). The reaction mixture contains all four deoxynucleotide triphosphates in concentrations of 0.2 mM. The reaction takes place at 15° C. for 30 minutes and is then stopped by heating at 65° C. for 10 minutes. The large fragment, or Klenow fragment, of DNA polymerase is used for fragments obtained by cutting with restriction endonucleases which generate 5'-protruding ends, such as EcoRI and BamHI. T4 DNA polymerase is used for fragments obtained by endonucleases which generate 3'-protruding ends, such as PstI and SacI. The use of these two enzymes is described on pages 113 to 121 of the Maniatis et al (1982) reference.

C. Agarose gel electrophoresis and purification of DNA fragments from gels

The agarose gel electrophoresis is carried out in a horizontal apparatus as described on pages 150 to 163 of the Maniatis et al. reference. The buffer used is the tris-acetate buffer described therein. The DNA fragments are stained by 0.5 µg/ml ethidium bromide which is normally already present in the gel during the electrophoresis or is added after the electrophoresis. The DNA is visualized by illumination with long-wavelength ultraviolet light.

When the fragments are to be removed from the gel, an agarose which gels at low temperature and can be obtained from Sigma Chemical, St. Louis, Mo., is used. After the electrophoresis, the required fragment is cut out, placed in a plastic tube, heated at 65° C. for about 15 minutes, extracted three times with phenol and precipitated twice with ethanol. This method is a slight modification of that described on page 170 of Maniatis et al (1982). Alternatively, the DNA can be isolated from the agarose with the aid of the Geneclean kit (Bio 101 Inc., La Jolla, Calif., USA).

D. Deletion of 5'-terminal phosphates frm DNA fragments

During the plasmid cloning steps, treatment of the vector plasmid with phosphatase reduces the recircularization of the vector (discussed on page 13 of the Maniatis et al reference). After the DNA has been cut with the correct restriction endonuclease, one unit of alkaline phosphatase from calf intestine, which was obtained from Boehringer-Mannheim, Mannheim, is added. The DNA is incubated at 37° C. for one hour and subsequently twice extracted with phenol and precipitated with ethanol.

E. Linkage of the DNA fragments

When it is intended to link together fragments with complementary cohesive ends, about 100 ng of each fragment are incubated in a reaction mixture of 20 to 40 µl with about 0.2 units of T4 DNA ligase from New England Biolabs in the buffer recommended by the manufacturer. The incubation is carried out at 15° C. for 1 to 20 hours. When it is intended to link DNA fragments with blunt ends, they are incubated as above except that the amount of T4 DNA ligase is increased from 2 to 4 units.

F. Transformation of DNA into E. coli

The E. coli strains HB101, W3101 and ED8767 are used for most experiments. DNA is inserted into E. coli by the calcium chloride method as described by Maniatis et al (1982), pages 250 to 251.

G. Screening of E. coli for plasmids

After the transformation, the resulting colonies E. coli are tested for the presence of the required plasmid by a rapid plasmid isolation method. Two customary methods are described on pages 366 to 369 of the Maniatis et al (1982) reference.

H. Isolation of plasmid DNA on a large scale

Methods for isolating plasmids from E. coli on a large scale are described on pages 88 to 94 of the Maniatis et al (1982) reference.

FIGURES

FIG. 1 [FIG. 1] shows a restriction map of the 6.4 (6.5) Kb PvuI fragment of the cosmid p98/1. The bar indicates the 1.8 kb SalI fragment and the striped region of the bar represents the sequenced SalI-BglIII subfragment.

Figure 2:
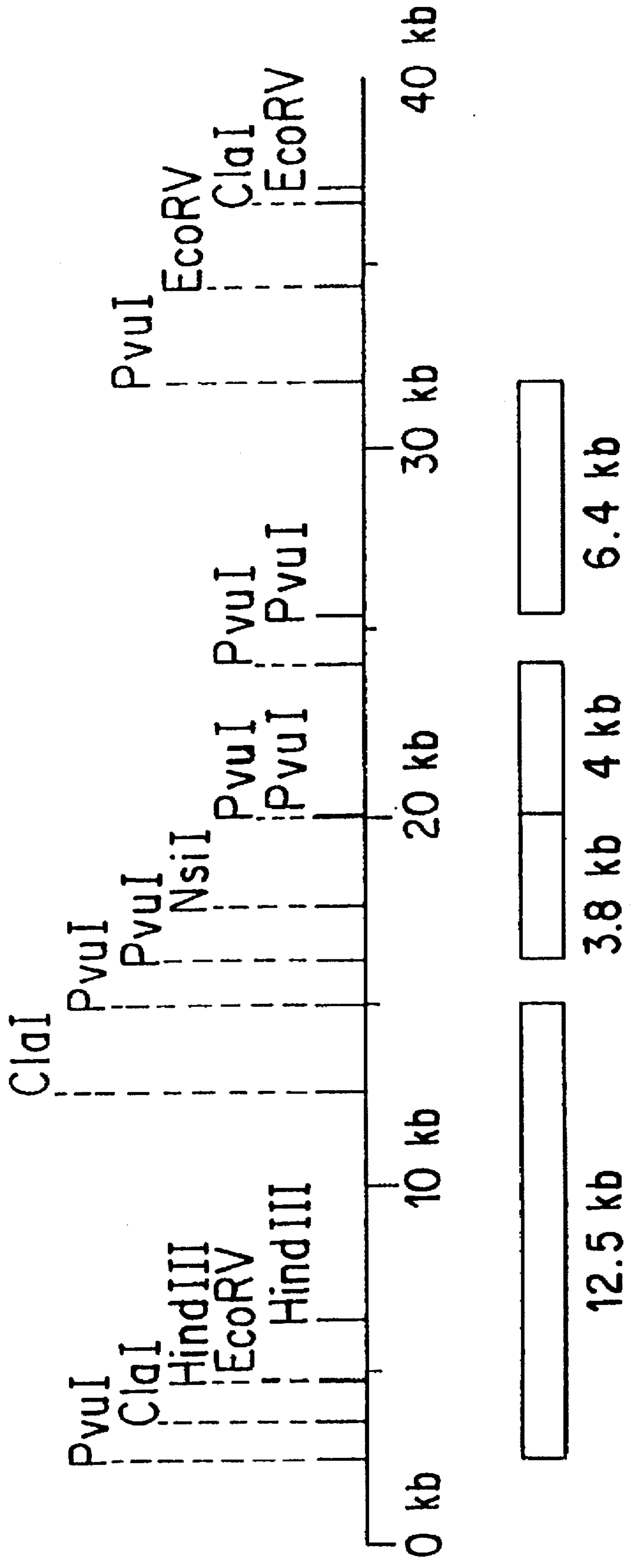

FIG. 2 [FIG. 2] shows the restriction map of the 40 Kb insert of cosmid p98/1. The bars indicate the position of the four PvuI fragments analyzed by gene disruption. Further PvuI sites outside of these PvuI fragments are not shown.

EXAMPLE 1

Cloning of a fragment from the 'soraphen gene duster' from *Sorangium cellulosum*

1.1 Construction of a cosmid gene bank from *Sorangium cellulosum*

1.1.1 Isolation of high molecular weight genomic DNA

The high molecular weight [about 100 Kb] genomic complete DNA of *Sorangium cellulosum* is isolated from the strain M15 with the aid of methods known per se.

This specifically entails initially *Sorangium cellulosum* cells being cultivated at a temperature of 28° C. in 200 ml of a G51b medium [see section: Media and buffers] with continuous agitation at 180 rpm for 10.days. The cells are subsequently removed by centrifugation at 10,000 rpm [Sorvall GSA Rotor; DuPont Instruments, Newton, Conn., USA] and resuspended in 36 ml of an STE buffer [see section: Media and buffers] to which lysozyme [Boehringer Mannheim, Mannheim, FRG] is added in a final concentration of 5 mg/ml. This mixture is incubated at 37° C. for 30 minutes. Subsequently, 16 ml of a lysing buffer [section: Media and buffers] are added and this new mixture is incubated at 55° C. for a further hour.

The cell lysate obtainable in this way is enriched with CsCl to a final concentration of 1 g/ml and this mixture is then centrifuged at 10,000 rpm [Sorvall SA600 Rotor; DuPont Instruments] for 10 minutes to remove particulate constituents. A further centrifugation of the lysate is carried out at 45,000 rpm [Beckman VTi50 Rotor; Beckman Instruments Inc., Palo Alto, USA] for a period of 18 hours and at a temperature of 20° C.

The genomic DNA can then be isolated from the readily visible, high viscosity fraction by, for example, simply puncturing the plastic centrifuge tube with the aid of a 16 gauge injection needle and allowing the contents to run out. The high viscosity fractions which comprise high molecular DNA are collected and subsequently combined.

This DNA-containing fraction is subsequently dialyzed extensively against TE buffer [see section: Media and buffers] and the DNA is concentrated by ethanol precipitation. The precipitate is centrifuged and the pellet is resuspended in 2 ml of TE buffer and stored at 40° C. until processed further.

1.1.2 Partial digestion of the high molecular weight DNA

The previously isolated DNA is subsequently digested with the aid of suitable restriction enzymes. In order to achieve different restriction levels therein, the DNA is subjected to three mutually independent partial digestions with Sau3A [Promega, Madison, Wis., USA] in a buffer solution also supplied by the manufacturer. The amount of DNA employed is in each case 100 μg, and the enzyme concentration is 0.04, 0.02 or 0.01 units/μg of DNA. The incubation time is 30 minutes at 37° C. The enzyme activity is stopped by adding $Na_2EDTA$ to a final concentration of 50 mM. This reaction mixture is extracted twice with phenol:chloroform [50:50] and once with chloroform, followed by an ethanol precipitation. The partially digested DNA is resuspended in TE buffer, and all samples are pooled and adjusted to a concentration of 1 mg/ml.

The DNA pretreated in this way is then heated at 65° C. for 5 minutes and fractionated according to size by centrifugation [Beckmann SW-28 Rotor; 25,000 rpm (82,700×g) at 20° C. for 16–18 hours] on a 10% to 40% strength sucrose density gradient [10%–40% sucrose in 5% steps in 1M NaCl, 20 mM tris [pH 8.0], 5 mM EDTA]. The gradients are fractionated in aliquots each of 0.5 ml, and samples of the order of 30 μl in size are removed from every second aliquot, dialyzed and analyzed together with a size standard on a 0.4% agarose gel.

1.1.3 Construction of a genomic gene bank

The cosmid vector pHC79 [Hohn B and Collins J, 1980] is completed digested with BamHI, extracted with phenol:chloroform [50:50] and subsequently precipitated and concentrated with ethanol.

Those fractions of the Sau3A partially digested *S. cellulosum* DNA which comprise DNA fragments with sizes of the order of 35 Kb to 45 Kb are pooled and concentrated via an ethanol precipitation.

This is followed by treatment with alkaline phosphatase from calf stomach [Promega], which is carried out in accordance with the manufacturer's instructions.

The ligation of the cosmid DNA to the *S. cellulosum* DNA which has been fractionated according to size is carried out with the aid of a T4 DNA ligase. This entails the two DNA starting materials being mixed together in approximately equimolar amounts [about 6 μg of *S. cellulosum* DNA and about 1 μg of vector DNA], followed by a heat treatment at 65° C. for 15 minutes and by a renewed ethanol precipitation. The final concentration of the complete DNA is 500 μg of DNA/ml to 800 μg of DNA/ml in a total volume of 10 μl. This reaction mixture is incubated first at room temperature for several hours and to follow at 15° C. for a further 10 to 14 hours.

One to two μl of the ligation mixture are then packaged in lambda phages using an in vitro commercial packaging kit which can be obtained, for example, from STRATAGENE, Inc. in La Jolla, Calif. (USA) or PROMEGA in Madison, Wis., USA. The resulting phage particles are used for infection of bacteria of a suitable $recA^-$ *E. coli* strain [for example of the *E. coli* strain HB 101]. The specific procedure for this is such that (a) the bacteria are first cultivated as overnight culture in a Luria broth medium [10 g/l Bacto tryptone; 5 g/l yeast extract; 5 g/l NaCl] supplemented with 0.4% maltose and 10 mM $MgSO_4$;

(b) the culture is diluted in the same medium and left to grow until an optical density [$OD_{600}$] of 0.5 [mid-log phase] is reached [about 2 hours];

(c) 0.2 ml of the *E. coli* culture is transferred into a sterile Eppendorf tube, 50 μl of the "packaged" phage particles are added, and the complete mixture is thoroughly mixed;

(d) after incubation at 37° C. for 15 minutes, 1 ml of Luria broth solution is added, and the incubation is continued for a further hour;

(e) to select transfected clones, aliquots of 0.1 ml are plated out on a Luria broth agar supplemented with 50 mg/l ampicillin; and (f) plasmid DNA is isolated with the aid of known methods from the colonies resulting after selection.

Titration of the phage material reveals a total of about 50,000 phage particles/ml.

1.2 Preparation of the radioactively labelled DNA probe from *S. violaceoruber* Tü22

Used as starting material for preparing the DNA probe is the plasmid pIJ5200 [Sherman et al, 1989] which comprises a 4.6 Kb BamHI fragment of the graI region [granaticin gene cluster ORF 1–4] of *Streptomyces violaceoruber* Tü22 cloned into the BamHI cleavage site of pUC18 [obtainable from GIBCO BRL, Basel, CH].

In order to obtain a DNA fragment which is free of DNA sequences which have homologies with corresponding pBR322 or pUC18 sequences, the 4.6 Kb BamHI fragment is first cloned into the streptomyces vector pIJ486 [Ward et al, 1986]. For this, about 3 μg of the plasmid pIJ5200 [Sherman et al, 1989] are completely cut with BamHI, and the resulting fragments are separated from one another by agarose gel electrophoresis.

The required 4.6 kb fragment is then removed from the agarose by electroelution. For this, it is first cut out as an approximately 2 mm to 3 mm wide agar strip from the agarose gel with a sterile scalpel and placed in a dialysis tube [prepared dialysis tubing ¼ inch diameter obtainable, for example, from BRL]. The dialysis tube containing the agarose block is then treated in 1×TAE buffer [iris-acetate 0.04M; EDTA 0.002M] in a horizontal agarose electrophoresis chamber with a current of 100 milliampere so that the current flows at right angles to the long axis of the dialysis tube for 2 hours. After reversal of the current for 45 seconds, the dialysis tube is opened and the contents (buffer and agarose block) are forced, using a 5 ml syringe, slowly through a glass fiber filter [Whatman GF/C; Whatman Scientific Ltd., Kent, GB]. The filter is then washed with 200 μl of TAE buffer [1×], and then tRNA [transfer RNA from baker's yeast, obtainable, for example, from Böhringer Mannheim, FRG] is added to a final concentration of 5 μl/ml to the filtered sample. The DNA sample is then extracted with phenol/chloroform [Maniatis et al, 1982, page 458] and precipitated with ethanol [Maniatis et al, 1982; page 461]. The resulting precipitate is taken up in 30 μl to 40 μl of TE buffer.

Approximately 0.5 μg of the fragment obtained in this way is mixed with about 0.1 μg of pIJ486 [Ward et al, 1986] vector DNA which is previously cut with BamHI, and is precipitated with ethanol [Maniatis et al, 1982; page 461] and ligated with T4 DNA ligase [obtainable from B öhringer Mannheim, FRG] in 20 μl of reaction buffer [as specified by manufacturer] at about 15° C. overnight. 2–5 μl of this ligation mixture are transformed into the *Streptomyces pilosus* strain M1/5 [Schupp et al, 1988] by the protoplast method described by Hopwood et al, (1985)]. The transformants are selected after incubation (28° C.) for 18 hours by pouring 4 ml of soft nutrient agar (Difco) which contains 250 μg/ml thiostrepton [see Schupp et al, 1985] onto the R2YE agar [Hopwood et al, 1988]. After incubation at 28° C. for 7 days, colonies are selected for isolation of plasmid DNA. The DNA isolation is carried out by a slight modification [according to Schupp et al, 1988] of the method of Birnboim and Doly (1979). The isolated plasmid DNA is subsequently digested with BamHI, and both digested and undigested DNA is analyzed with the aid of gel electrophoresis.

The colonies which possessed an additional BamHI fragment of 4.6 Kb are cultivated in 500 ml of a 148G medium [Schupp et al, 1986], and the plasmid DNA is isolated with the aid of the CsCl gradient methods [Hopwood et al, 1985]. The plasmids obtainable in the manner described previously and having the 4.6 Kb BamHI fragment of *S. violaceoruber* are called p82/11 and p82/21.

For radioactive labeling of the 4.6 Kb DNA fragment, about 1 ug of the plasmid p82/21 is completely cut with BamHI, and the fragments obtained in this way are separated from one another by agarose gel electrophoresis. The 4.6 Kb fragment is subsequently isolated from the agarose gel by electroelution (see above). Approximately 0.2 μg of the 4.6 Kb BamHI fragment isolated in this way is employed for the radioactive labeling by means of a nick translation [Rigby D. W. J. et al, 1977]. The nick translation can be carried out using the nick translation's system commercially available from GIBCO BRL (Bethesda Research Laboratories Life Technologies Inc.) in Basle, CH, with the labeling taking place, according to the manufacturer's instructions, with 80 ZμCi of d-CTP $^{32}P$. The labelled 4.6 Kb fragment can be separated from the non-incorporated nucleotides by passage through a nick ™column containing Sephadex G-50 [Pharmacia Biosystems, Dübendorf, CH] and subsequent elution of 200 μl fractions with TE buffer.

1.3 Hybridization of individual clones within the cosmid gene bank of *Sorangium-cellulosum* using the DNA probe from *S. violaceoruber*

It is possible by infection of bacteria of the *E. coli* strain HB101 with 100 μl of in vitro packaged lambda phages [according to Example 1.1], after plating on Petri dishes with LB agar supplemented with ampicillin [60 μg/ml], to obtain a large number [up to 1300 colonies and more] of ampicillin-resistant colonies. These colonies can be tested by means of colony hybridization on nylon filters in the following way [Amersham instructions for Hybond filters]:

A nylon filter [Amersham Transfer Membrane Hybond-N; Amersham International, Amersham, UK] is placed on the colonies, and after one minute, —with the colonies upwards—, placed on a sterile filter paper [Whatman No.3]. To produce an imprint (replica) of the colonies, a second filter is pressed onto the first and subsequently placed on LB agar plates [supplemented with 60 μg/ml ampicillin] and incubated thereon at 37° C. until the colonies have a diameter of about 1 mm. The first filter is then, with the colonies upwards, placed on a stack of a total of 5 Whatman No.3 papers impregnated with a denaturation solution [1.5M NaCl; 0.5M NaOH]. After acting for 7 minutes, the filters are placed in the same way on a new filter impregnated this time with a neutralization solution [1.5M NaCl; 0.5M Tris-HCl (pH 7.2); 0.001M EDTA]. This solution is allowed to act for 3 minutes before the treatment with the neutralization solution is repeated once more.

The filters are then briefly immersed in 2×SSC [0.3M NaCl; 0.03M sodium citrate (Maniatis et al, 1982] and, for drying, placed on dry Whatman No.3 filters (colonies upwards) and dried in air. In order to fix the DNA, the filters are wrapped in Saran film [Dow Chemical Company] and irradiated with UV light (312 nm) in a UV transilluminator [CAMAG Reprostar, Camag, Muttenz, CH] for 5 minutes (colonies downwards).

Subsequently, for the prehybridization, the filters are incubated at 65° C. for 90 min with a buffer of the following composition: 2×SSC [Maniatis et al, 1982+1×Denhard [Maniatis et al, 1982]+0.5% SDS+50 μg/ml salmon sperm DNA [DNA sodium salt, Type III, from Salmon Testes; SIGMA Chemical Co., St. Louis, USA] (denatured by heating at 100° C. for 10 min.) For the hybridization, about $2\times10^5$ cpm/ml of the 4.6 Kb DNA fragment, labelled by nick translation, from plasmid pCT82/21 [see Example 1.2], which has previously been denatured by heating at 100° C. for 10 min., are added.

The actual hybridization then takes place at 65° C. for 24 hours.

After the hybridization, the filter is washed first in 2×SSC at room temperature for 15 min, then in 2×SSC at 60° C. for 15 min, subsequently in 2×SSC+0.1% SDS at 60° C. for 30 min and finally in 0.5×SSC at 60° C. for 15 min. The subsequent autoradiography is carried out with X-ray film [for example Fuji RX (medical X-ray film)] for 24 hours.

1.4 Analysis of the cosmid-containing colonies by means of plasmid isolation and Southern hybridination The cosmid clones obtaininable by the previously described method and showing the strongest signals in the colony hybridization are transferred from the agar plate into 2 ml of LB medium and incubated at 37° C. overnight. A 1 ml aliquot of these cultures is then used for isolating the plasmid DNA [as described by Maniatis et al, (1982); pages 368–369].

The isolated plasmids are then digested with SalI, and the fragments obtained in this way are fractionated in a 0.8% tris-acetate agarose gel [1×TAE] at 1.2 volt/cm for 15 hours. The gel is subsequently treated first for 2×15 minutes in a denaturing solution [1.5M NaCI; 0.5M NaOH] and subsequently for 2×15 minutes in a neutralizing solution [1.5M NaCl; 0.5M Tris-HCl; 1 mM EDTANa2 (pH 7.2)] shaking gently at room temperature. The DNA is then transferred by means of a Southern capillary blotting [Maniatis et al, 1982; pages 383–386] using 10-fold concentrated SSC buffer to a nitrocellulose membrane [0.45μ nitrocellulose; Bio-Rad Laboratories, Richmond, USA] and subsequently fixed on the membrane at 80° C. in vacuo for 2 hours.

For the subsequent hybridization, the filter is first incubated for the prehybridization at 65° C. for 120 min with a buffer of the following composition: 2×SSC (Maniatis et al, 1982) +1×Denhard (Maniatis et al, 1982)+0.5% SDS+50 μg/ml salmon sperm DNA (denatured by heating at 100° C. for 10 min.). For the actual hybridization, about $8\times10^6$ cpm of the 4.6 Kb DNA fragment labelled by nick translation from the plasmid p82/21 [see Example 1.2], which is previously denatured by heating at 100° C. for 10 min, are added. The hybridization then took place at 65° C. for 36 hours.

After the hybridization, the filter is washed twice in 2×SSC+0.1% SDS at 55° C. for 20 min and then in 0.2×SSC+0.1% SDS at the same temperature for 20 min. The subsequent autoradiography is carried out by means of an X-ray film [for example Fuji RX (medical X-ray film)] for 48 hours.

A cosmid [p98/1)] which shows a strong band of 1.8 Kb in the autoradiograph is selected for further work.

1.5 Subcloning of the 1.8 kb SalI fragment from cosmid p98/1 into the *E. coli* vector pBR322

For preparation of a larger amount of the cosmid p98/1, a 20 ml culture of the corresponding *E. coli* strain HB101/p98/1 [see Example 1.1] is prepared in an LB medium and incubated overnight. It is then possible to isolate a larger amount of DNA of cosmid p98/1 from this culture [15 ml] [see Maniatis et al, (1982); pages 368–369].

About 3 μg of the cosmid p98/1 DNA are completed digested with SalI, and the fragments obtainable in this way are fractionated by electrophoresis on a 0.8% tris-acetate agarose gel [1×TAE] at 1.2 volt/cm for 15 hours. The required 1.8 Kb DNA fragment is then removed from the agarose by electroelution in analogy to the procedure described in Example 1.2.

30 μl of the sample of the 1.8 Kb SalI fragment obtained in this way are mixed with about 0.05 μg of the plasmid pBR322 which has previously been cut with SalI, and are precipitated with ethanol [Maniatis et al, (1982); page 461] and then ligated with T4 DNA ligase [Böhringer Mannheim, FRG] in 20 μl of reaction buffer [as specified by manufacturer] at about 15° C. overnight.

The resulting ligated DNA [5 μl] is subsequently cloned into cells of the *E. coli* strain HB101 which have been made competent as described by Maniatis et al (1982) [pages 250–251] and plated out on LB agar which is supplemented with 50 μg/ml ampicillin.

Tetracycline-sensitive colonies can be found by differential screening of the resulting transformed colonies on LB agar with 50 μg/ml ampicillin or with 50 μg/ml ampicillin and 20 μg/ml tetracycline, and their plasmid DNA can be isolated [as described by Maniatis et al, 1982; pages 368–369]. The isolated plasmid DNA is then cut with SalI and analyzed by agarose gel electrophoresis for the size of its inserted fragments, employing as comparison the cosmid p98/1 which is also applied.

A plasmid [p102/III2] which comprises an additional fragment of the required size can then be isolated from the gel in the manner previously described. The identity of this additional fragment to the 1.8 Kb SalI fragment from the cosmid p98/1 can then be confirmed in a Southern transfer [as described in Example 1.4] and hybridization with the 4.6 Kb BamHI DNA probe from *S. violaceoruber.*

1.6 Sequencing of a 0.78 Kb SalI/BglII subfragment of the 1.8 Kb SalI fragment of plasmid p108/III2.

For the sequencing, the 1.8 kb SalI fragment is first isolated from the plasmid p108/III2 described in Example 1.5. For this, about 2 μg of the plasmid p108/III2 are completely cut with SalI and fractionated by electrophoresis in a 0.8% tris-acetate agarose gel at 1.2 volt/cm for 15 hours. The 1.8 kb SalI fragment is then isolated by electroelution in analogy to the procedure described in Example 1.5.

The SalI fragment [about 0.3 μg) can subsequently be ligated directly into the SalI cleavage site of the vector M13mp18 [about 0.02 μg].

As an alternative to this, the SalI fragment can also be additionally cut with BglII and ligated in the form of two BglII-SalI subfragments [2 fragments, total about 0.3 μg] into the vector M13mp19 which is previously cut with SalI and BamHI [about 0.1 μg] [the ligation with T4 DNA ligase can be carried out as described in Example 1.5]. The M13mp18 and M13mp19 vectors are commercially available from GIBCO-BRL (Basle, CH). The cloning into these vectors and the subsequent transfection of *E. coli* JM101 cells can be carried out by the method described by Maniatis et al (1989) [page 4.35–4.38].

In each case 12 of the recombinant phage plaques (colorless) obtained in this way are isolated as described by Maniatis et al [page 4.25; (1989)] and replicated in *E. coli* JM101. Analysis of the recombinant phages for an insert fragment of the correct size can likewise be carried out by means of known methods using gel electrophoresis [Maniatis et al [page 4.39–4.40; (1989)]. A larger amount of the single-stranded DNA from the phages with the required insert is then isolated [Maniatis et al [page 4.29–4.30; (1989)].

The DNA sequencing can be carried out with the aid of the T7 sequencing kit from Pharmacia by the dideoxy method of Sanger (1977). For this, the previously isolated single-stranded DNA is employed as template. All sequencing operations are carried out in accordance with the instructions of the Pharmacia T7 sequencing kit (1991 instructions, No. xy-010-00-08) using the universal primer contained in the kit and the $^{35}S$ dATP [Amersham International; Amersham, UK] which is used for the radioactive labeling. The samples obtainable in this way are subsequently fractionated by electrophoresis on a denaturing polyacrylamide gel (6%) and examined by autoradiography with an X-ray film [Kodak X-OmatS]. Details of the procedure can be found in the instructions of Maniatis et al [page 13.45–13.58; (1989)].

4 oligonucleotides are synthesized on the basis of the DNA sequence information obtained above in order to determine the DNA sequence in the central region of the two SalI-BglII subfragments.

The oligonucleotides Oli1 and Oli2 can be employed as primers for the sequencing in the following sequencing strategy to sequence the 5'-located SalI/BglII subfragment. The 2 oligonucleotides have the following base sequence:

| | |
|---|---|
| 5' TAC TGG TAT CGA AAC CT 3' | (151–167) = Oli1 (SEQ ID NO: 2) |
| 5' GAA GAC GAC GTG GTC TT 3' | (642–626) = Oli2 (SEQ ID NO: 3) |

The sequencing strategy for the 0.78 Kb SalI/BglII fragment can be depicted diagrammatically as follows:

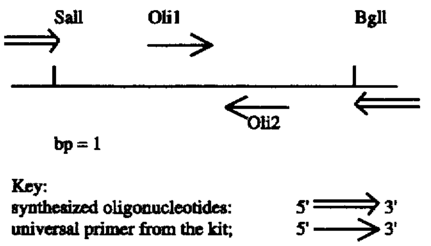

2. Subcloning of PvuI fragments of the cosmid p98/1 and conjuative transfer into *S. cellulosum*

Since the vector pSUP2021 which is used for the gene disruption experiment described in Example 3 has a unique PvuI cleavage site in the $Amp^R$ gene, PvuI fragments are correspondingly used hereinafter for the subcloning steps and the conjugative transfer.

2.1 Subcloning of PvuI fragments of the cosmid p98/1 into the plasmid pSUP2021

Cosmid p98/1 [about 4 μg] is completely cut with PvuI, and the resulting fragments are fractionated by electrophoresis on a 0.8% tris-acetate agarose gel [1×TAE buffer] at 1.2 volt/cm for 18 hours (FIG. 2) in analogy to the procedure described in Example 1.5.

The well-separated fragments [about 6.5 Kb, about 10 Kb and a fraction of 4 Kb and 4.2 Kb] are isolated by electroelution by the method described in Example 1.5 and each resuspended in 40 μl of TE buffer. 35 μl of each of the samples obtainable in this way of the 4 fragments are mixed with about 0.05 μg of the plasmid pSUP2021 [Simon R et al, 1983] which is previously cut with PvuI, precipitated with ethanol [as described by Maniatis et al (1982); page 461] and subsequently ligated with T4 DNA ligase [obtainable from Böhringer, Mannheim, FRG] in 20 μl of reaction buffer at about 15° C. overnight.

*E. coli* HB101 cells made competent as described by Maniatis et al (1982) are transformed [Maniatis et al (1982); page 250–251] with in each case 10 μl of the 3 DNA samples obtainable from the ligase reaction described above, and plated out on LB agar with 30 μg/ml chloramphenicol. Each of the colonies transformed in this way is tested for its ampicillin sensitivity. The ampicillin-sensitive colonies are subsequently identified and used as starting material for isolating the plasmid DNA [Maniatis et al (1982); pages 368–369]. The isolated plasmids are then cut with Pvul and analyzed by an agarose gel electrophoresis. Cosmid p98/1 cut with PvuI is used as comparison standard. It is possible in this way to identify a total of three plasmids which comprise the required fragment. The plasmid with the fragment comprising about 6.5 Kb is called pSN 105/7. The plasmid with the fragment comprising about 10 Kb is called pSN120/10. The plasmids with the fragments comprising 4 Kb and 4.2 Kb are called pSN120/43–49 and pSN120/46 respectively contained fragments 4 and 4.2 kb in size.

An exact measurement of the above mentioned fragments turns out the following sizes:

| size used in the text [Kb] | exact size as measured [Kb] | plasmid name |
|---|---|---|
| 10 | 12.5 | pSN120/10 |
| 6.5 | 6.4 | pSN105/7 |
| 4.2 | 4 | pSN120/43–49 |
| 4 | 3.8 | pSN120/46 |

2.2 Conjugal transfer of recombinant plasmids into *S. cellulosum*

2.2.1 Transformation of plasmids pSN105/7, pSN120/10, pSN120/43-49 and pSN120/46 into *E. coli*

The plasmids pSN105/7, pSN120/10, pSN120/43-49 and pSN120/46, whose preparation and isolation has previously been described in Example 7.1, are transformed into the *E. coli* strain ED8767 which comprises the helper plasmid pUZ8 [Hedges R. W. and Matthew M (1979)].

The plasmid pUZ8 is a derivative of the plasmid RP4 which comprises a wide host range and which is described by Datta et al (1971). The modifications compared with the initial RP4 plasmid essentially relate to the ampicillin-resistance gene and to the insertion element IS21, both of which are deleted, and to the incorporation of an additional gene which confers resistance to mercury ions [see Jaoua et al (1987)].

The colonies resulting after transformation and subsequent incubation on LB agar supplemented with tetracycline [10 μg/ml] and chloramphenicol [25 μg/ml] for 24 hours are subjected to a differential screening by parallel plating out on ampicillin-containing [60 μg/ml] and ampicillin-free medium. It is subsequently possible to isolate those colonies which, because of the integration of the Sorangium DNA fragments, have lost their ampicillin resistance. The cultures obtainable in this way can then be employed directly as donor cells for the conjugative transfer of the recombinant plasmids into *Sorangium cellulosum* cells.

2.2.2 Conjugative transfer

For the actual transfer, 15 ml of a *Sorangium cellulosum* SJ3 culture in the stationary phase [$1–4\times10^9$ cells/ml] are mixed with 10 ml of a late-log phase culture of *E. coli* ED8767 donor cells which comprise a comparable number of cells. These are then centrifuged together at 4000 rpm for 10 minutes and resuspended in 500 μl of a G51b or G51t medium.

It proves advantageous in this case to expose the Sorangium recipient cells to a brief heat treatment in a water bath before the conjugation with *E. coli*. The best transfer results with the *Sorangium cellulosum* strain SJ3 can be achieved with a heat treatment at a temperature of 50° C. for 10 minutes. Transfer frequencies of $1–5\times10^{-5}$ can be achieved under these conditions, which corresponds to an increase by a factor of 10 compared with a method without previous heat treatment.

Transfer to plates with SolE solid medium is followed by incubation at 30° C. for two days. The cells are then harvested and resuspended in 1 ml of G51b or G51t medium. 100 μl of this bacterial suspension are plated out on a selective SolE medium which, besides kanamycin [25 mg/l], also contains phleomycin [20 to 35 mg/l] and streptomycin [300 mg/l] as selective agents. The counter-selection of the donor strains [*E. coli* W3101 (pME305)] takes place with the aid of streptomycin.

The colonies which have grown on this selective SolE medium after an incubation time of 10 to 14 days at a temperature of 30° C. are transconjugants of *Sorangium cellulosum* which have acquired phleomycin resistance by conjugative transfer of the plasmids pSN105/7, pSN120/10, pSN120/43–49 and pSN120/46. These phleomycin-resistant colonies can be used for the subsequent molecular biological investigations. The transformation frequency for the transfer of the plasmid DNA to Sorangium averages $1–3\times10^{-6}$ based on the SJ3 recipient strain.

3. Characterization of the previously identified fragments 3.1 Assignment of the 1.8 Kb SalI fragment into the 6.5 Kb PvuI fragment of cosmid p98.1

The plasmids pSN105/7, pSN120/10, pSN120/43–49 and pSN120/46, whose preparation and isolation has been described in Example 2.1, are completely digested with SalI and PvuI, and the fragments are fractionated on a 0.8% tris-acetate agarose gel as in Example 1.4 and transferred by Southern capillary blotting onto a nitrocellulose membrane. The hybridization is carried out using the 1.8 Kb SalI fragment of plasmid p108/III2 as probe, under the conditions described in Example 1.4, carrying out the last filter washing step at 65° C. (in 0.2×SSC+0.1% SDS).

Evaluation of the agarose gel and of the autoradiograph shows that the clone pSN105/7 comprises in its PvuI fragment which comprises 6.5 Kb a 1.8 Kb SalI fragment which is identical to the 1.8 Kb fragment cloned into the plasmid p108/112.

3.2 Characterization of the 6.5 Kb PvuI fragment of cosmid p98/1 by restriction cleavage sites The plasmid pSN105/7 is digested with PvuI as described in Example 3.1, and the two fragments obtained in this way are fractionated on a 0.8% tri-acetate agaros gel [1×TAE] at 1.2 volt/cm for 15 hours. The DNA fragment which is 6.5 Kb in size is then removed from the gel by electroelution in analogy to the procedure described in Example 1.2 and taken up in 30 μl of TE buffer.

To characterize the 6.5 Kb PvuI fragment by restriction cleavage sites, the resulting 6.5 Kb DNA fragment is digested with, in each case independently of one another, BglII, SphI and SmaI as well as completely, and the size of the resulting fragments is determined after fractionation on a tris-acetate agarose gel [1×TAG]. For this, HindIII-cut λ

DNA (obtainable from GIBCO-BRL, Basle, Switzerland) is employed as standard for comparison of sizes of the DNA fragments on the same gel. In order to be able to establish unambiguously the position of the individual fragments with respect to one another, the 6.5 Kb fragment is additionally digested with all conceivable combination of two of the abovementioned restriction enzymes in each case.

Digestion with BglII yields two fragments 4.3 Kb and 2.3 Kb in size, and that with SphI yields 4 fragments 2.8 Kb, 1.5 Kb, 1.5 Kb and 0.7 Kb in size. Digestion with SmaI yields 3 fragments 2.9 Kb, 2.0 Kb and 1.6 Kb in size. In this case the actual size of the fragments may differ by ±10% from the stated value because of the method of measurement used. The position of the BglII and SphI cleavage sites on the 6.5 Kb fragment of cosmid p98/1 can be established on the basis of the fragment sizes found as depicted in FIG. 1.

4. Function test 4.1 Analysis of the effect of the PvuI fragment of the cosmid p98/1 on the soraphen production by *S. cellulosum* after gene disruption Transfer of plasmids comprise DNA sections which are homologous with corresponding sections within the *Sorangium cellulosum* genome leads to integration of said DNA sections into the chromosomal *Sorangium cellulosum* DNA at the site of the homology via homologous recombination.

If the homologous region is a section within a gene cluster, for example that for soraphen biosynthesis, the plasmid integration leads to inactivation of this cluster by so-called gene disruption. This method thus allows the function of a cloned DNA fragment in *Sorangium cellulosum* to be analyzed.

To check the function of the PvuI fragments of cosmid p98/1, well-grown, transconjugant colonies [see Example 2.2.2] are removed from the master plates with a sterile plastic loop and streaked on a selective So1E medium which contains kanamycin [25 mg/l], phleomycin [20–35 mg/l] and streptomycin [300 mg/l] as selective agents. After an incubation time [at 30° C.] of 8 10 days, about $1-2\times10^9$ cells are removed with a sterile plastic loop and transferred into 2 ml of G-55 medium [without resin].

After incubation at 30° C. and 180 rpm for 3–4 days, samples each of 1 ml [$1\times4\times10^9$ cells/ml] are transferred into an Erlenmeyer flask with 10 ml of G55 medium [without resin]. After an incubation under identical conditions for a further 3–4 days, another transfer is carried out [5 ml; $1-4\times10^9$ cells/ml] but this time into a G55 medium [50 ml] which additionally contains an adsorber resin such as, for example, AMBERLITE XAD-1180® [ROHM & HAAS DEUTSCHLAND GmbH, Frankfurt, FRG]. Quantitative determination of the soraphen produced takes place after incubation at 30° C. and 180 rpm for 7 days.

The soraphen determination is carried out with the aid of HPLC analysis. This entails the cultures initially being filtered with suction through a polyester filter [Sartorius, B 420-47-N]. The resin remaining on the filter is then resuspended in 50 ml of isopropanol and extracted at 30° C. and 180 rpm for one hour. 1 ml is removed from this suspension and centrifuged at 12,000 rpm in an Eppendort Microfuge. 200 μl of the supernatant are diluted with 600 μl of isopropanol, and the amount of soraphen contained therein is determined by means of an HPLC with UV detector. The detection wavelength is at 210 nm.

In total, 35 different transconjugants with integrated pSN105/7 plasmid, 14 transconjugants with pSn120/10 plasmid, 18 transconjugants with pSN120/43-49 plasmid and 8 transconjugants with pSN120/46 plasmid were tested in the manner described previously.

HPLC analysis revealed in this case that all the transconjugants no longer produce soraphen. By contrast, soraphen A was detectable in a concentration of 50–100 mg/l with the positive controls, with the SJ3 recipient strain and with the transconjugant strain with the recombinant plasmid pSJB55.

This means that, after integration into the chromosomal *Sorangium cellulosum* DNA, all 4 PvuI fragments unambiguously block soraphen production. These fragments thus comprise a part of the genes which are involved directly or indirectly in soraphen synthesis.

5. Identification of the 'soraphen gene duster'

5.1 Isolation of cosmid clones with overlapping inserts

Clones which yield with fragments of the insert of p98/1 a strong hybridization signal are selected with the aid of colony hybridization according to the method described under 1.3 from the cosmid gene bank produced as in Example 1.1. Used as hybridization probe is either the radioactively labelled 1.8 Kb fragment of p98/1 or else preferably selected SalI fragments which can be assigned on the basis of the distribution of the SalI fragments in the sorangium part of p98/1 to the left or right flanking zones of the insert of p98/1.

5.2 Confirmation of the overlap of novel cosmids with p98/1

It is possible by hybridization analysis to identify fragments which overlap the insert from p98/1 in the 3' or 5' direction. These are isolated and employed for the subsequent walking steps.

The hybridization analysis comprises the following specific steps:

The plasmid DNA is isolated by the method described in Example 1.4 from the cosmid clones which show a strong signal in the method described previously [compare 1.4]. The isolated plasmids are then digested with SalI and, in parallel, with PvuI, and the fragments obtained in this way are fractionated on an agarose gel and subsequently transferred by means of Southern capillary blotting [Maniatis et al, 1982; pages 383-386] to a nitrocellulose membrane.

It is possible by hybridization of the filter with the 1.8 Kb SalI fragment or with a SalI fragment from the flanking zone of the insert of p98/1 as probe for the overlap of the novel cosmid clones to be confirmed and assigned to the right or left side of the insert of p98/1. The methods mentioned here can be carried out exactly in accordance with the techniques described under 1.4.

The number of common SalI and PvuI fragments found in the plasmid p98/1 and the novel cosmid clones provides further information about the size of the overlaps in the insert region. It is possible, where appropriate, to isolate further cosmids with regions of the *Sorangium cellulosum* chromosome which are located even further left or right of the insert fragment from plasmid p98/1. For this, the above procedure is repeated with a SalI fragment of a "right" or "left" cosmid relative to the p98/1 insert as probe.

5.3. Function analysis

The adjacent and overlapping DNA fragments identified in the manner described above are examined for their function in soraphen biosynthesis within the scope of a 'gene disruption' as described in Examples 2.1–2.2.2. The walking process with novel cosmids is continued until fragments which have no effect on soraphen production and are thus located outside the 'soraphen gene cluster' are reached. It is possible in this way to locate and clone the complete gene cluster which comprises the insert from cosmid p98/1.

5.4. Mapping of the restriction fragments

It is possible by restriction mapping to establish the sequence of the resulting restriction fragments and thus to construct an accurate restriction map of the complete region. In parallel with this, the DNA sequence of the individual fragments is determined by the procedure described in Example 1.6.

DEPOSITION

The following microorganisms and plasmids have been deposited within the scope of the present application at the "Deutsche Sammlung von Mikroorganismen und Zellkulturen GmbH", which is recognized as international depository in accordance with the Budapest Treaty, in Braunschweig (FRG) in compliance with the requirements of the Budapest Treaty on the international recognition of the deposit of microorganisms for the purposes of patent procedure.

| Microorganism/ Plasmid | Date of deposit | Deposit number |
|---|---|---|
| pSN105/7 cloned in *E. coli* | 25.08.1992 | DSM 7217 |

The following microorganisms and plasmids have been deposited within the scope of the present application at the Agricultural Research Culture Collection (NRRL), 1815N. University Street, Peoria, Ill. 61604, which is recognized as international depository in accordance with the Budapest Treaty, in compliance with the requirements of the Budapest Treaty on the international recognition of the deposit of microorganisms for the purposes of patent procedure.

| Microorganism/ Plasmid | Date of deposit | Deposit number |
|---|---|---|
| p98/1 cloned in *E. coli* HB101 | May 20, 1994 | NRRL B-21255 |

| MEDIA AND BUFFER SOLUTIONS | |
|---|---|
| G51b Medium (pH 7.4) | |
| Glucose | 0.2% |
| Starch | 0.5 % |
| [potato starch, Noredux type; CERESTAR ITALIA S.p.a., Milan, Italy] | |
| Peptone [DIFCO Laboratories, USA] | 0.2% |
| Probion S | 0.1% |
| [Single Cell Protein; HÖCHST AG, Frankfurt, FRG] | |
| $CaCl_2 \times 2\ H_2O$ | 0.05% |
| $MgSO_4 \times 7\ H_2O$ | 0.05% |
| HEPES [FLUKA] | 1.2% |
| G51t Medium (pH 7.4) | |
| Glucose | 0.2% |
| Starch | 0.5% |
| [potato starch, Noredux type; CERESTAR ITALIA S.p.a., Milan, Italy] | |
| Tryptone [MARCO, Hackensack, NJ USA] | 0.2% |
| Probion S | 0.1% |
| [Single Cell Protein; HÖCHST AG, Frankfurt, FRG] | |
| $CaCl_2 \times 2\ H_2O$ | 0.05% |
| $MgSO_4 \times 7\ H_2O$ | 0.05% |
| HEPES [FLUKA] | 1.2% |
| G52c Medium (pH 7.4) | |
| Glucose | 2.0 gl |
| Starch | 8.0 gl |
| [potato starch, Noredux type; CERESTAR ITALIA S.p.a., Milan, Italy] | |

-continued

| MEDIA AND BUFFER SOLUTIONS | |
|---|---|
| Soybean flour deoiled | 2.0 g/l |
| [MUCEDOLA S.r.l., Settimo Milanese, Italy] | |
| Yeast extract | 2.0 g/l |
| [FOULD & SPRINGER, Maison Alfort, France] | |
| $CaCl_2 \times 2\ H_2O$ | 1.0 g/l |
| $MgSO_4 \times 7\ H_2O$ | 1.0 g/l |
| Fe-EDTA [8 g/l stock solution] | 1.0 ml |
| HEPES [FLUKA] | 2.0 g/l |
| Distilled water ad | 1000 ml |
| pH is adjusted to 7.4 with NaOH before sterilization [120° C. for 20 minutes]. pH after sterilization: 7.4. | |
| Medium: G-55 200 mlflask with 50 ml of medium | |
| Starch | 8.0 g/l |
| [potato starch, Noredux type; CERESTAR ITALIA S.p.a., Milan, Italy] | |
| Dextrin from potatoes [supplied by Blattmann, Wädenswil, CH] | 8.0 g/l |
| Glucose | 2.0 g/l |
| Soybean flour deoiled | 2.0 g/l |
| [MUCEDOLA S.r.l., Settimo Milanese, Italy] | |
| Yeast extract | 2.0 g/l |
| [FOULD & SPRINGER, Maison Alfort, France] | |
| DL-aspartic acid ($C_4H_7NO_7$) | 1.0 g/l |
| $CaCl_2 \times 2H_2O$ | 1.0 g/l |
| $MgSO_4 \times 7H_2O$ | 1.0 g/l |
| HEPES (Fluka No. 54461) | 12.0 g/l |
| Fe-EDTA (8 g/l stock solution) | 1.0 g/l |
| MZM 1 (resin) | 50.0 ml/l |
| Tap water ad 1000 ml | |
| pH before ster.: adjust to 7.5 with NaOH | |
| pH after ster.: 7.4–7.5 | |
| Inoculum: 5 ml of a well-grown culture [ca 1–4 × $10^9$ cells/ml] | |
| SolE Medium (pH 7.4) | |
| Glucose* | 0.35% |
| Tryptone [MARCO, Hackensack, NJ USA] | 0.05% |
| $MgSO_4 \times 7\ H_2O$ | 0.15% |
| Ammonium sulfate* | 0.05% |
| $CaCl_2 \times 2\ H_2O$* | 0.1% |
| $K_2HPO_4$* | 0.006% |
| Sodium dithionite* | 0.01% |
| Fe-EDTA* | 0.0008% |
| HEPES [FLUKA] | 1.2% |
| Supernatant of a sterilized, stationary *S. cellulosum* culture* | 3.5% (v/v) |
| Agar | 1.5% |
| LB Medium | |
| Tryptone | 10.0 g.l |
| Yeast extract | 5.0 g/l |
| NaCl | 5.0 g/l |
| STE buffer (pH 8.0) | |
| Sucrose | 25% |
| EDTANa2 | 1 mM |
| Tris-HCl | 10 mM |
| RLM buffer (pH 7.6) | |
| SDS | 5% |
| EDTANa2 | 125 mM |
| Tris-HCl | 0.5 mM |
| TER buffer | |
| Tris-HCl (pH 8.0) | 10 mM |
| 1 mM EDTANa2 | 1 mM |
| RNAse | 10 μg/ml |
| Litigation buffer | |
| $MgCl_2$ | 0.1 M |
| Tris-HCl (pH 7.8) | 0.5 M |
| Lysing buffer [pH 7.6] | |
| Na-sarkosyl | 5% |
| $Na_2$-EDTA | 125 mM |
| Tris-HCl | 0.5 M |

-continued

| MEDIA AND BUFFER SOLUTIONS | |
|---|---|
| TE buffer | |
| Tris-HCl [pH 8.0] | 10 mM |
| $Na_2EDTA$ | 1 mM |

*Addition takes place only after sterilization pH is adjusted to 7.4 with NaOH before sterilization [120° C. for 20 minutes]

LIST OF REFERENCES

Bibb M. et al, Gene 30, 157–166, 1984
Birnboim und Doly, Nucl Acids Res 7, 1513–1523, 1979
Breton A. M. et al, J Bacteriol, 161: 523–528 (1985)
Breton A. M. et al, J Biotechnol, 4: 303–311 (1986)
Breton A. M. und Guespin-Michel J. F., FEMS Microbiol Lett, 40: 183–188 (1987)
Datta N. et al, J Bacteriol 108: 1244–1249 (1971)
Haymes B. T. et al, Nucleic Acid Hybridisation a Practical Approach, IRL Press, Oxford, England (1985)
Hedges R. W. and Matthew M., Plasmid 2, 269–278, 1979
Hohn B. und Collins J., Gene 11, 291, 1980
Hopwood et al, "Genetic Manipulation of Streptomyces a Laboratory Manual"; The John Innes Foundation, Norwich UK, 1985
Jaoua S. et al, Plasmid 18: 111–119 (1987 )
Jaoua S. et al, Plasmid 23: 183–193 (1990)
Jaoua S. et al, Plasmid 28: 157–165 (1992)
Kaiser D., Genetics of Myxobacteria, in: "Myxobacteria: Development and Cell Interactions", ed E. Rosenberg, pp 163–184, Springer Verlag, Berlin/New York (1984);
Kuner J. M. und Kaiser D., Proc Natl Acad Sci USA, 78: 425–429 (1981)
Kuspa und Kaiser, J Bacteriol Vol 171 (5), 2762–2772 (1989)]
Malpartida und Hopwood [Nature 309, 462–464, 1984].
Maxam and Gilbert, 'Sequencing end-labelled DNA with base-specific chemical cleavage', in: Methods in Enzymology 65: 499–560, Academic Press, New York, London, (1980).
Maniatis T., Molecular Cloning, A Laboratory Manual, Cold Spring Harbor Press, Cold Spring Habor, N.Y. (1982)
O'Conner K. A. und Zusman D. R., J Bacteriol, 155: 317–329 (1983)
Reichenbach et al, Trends in Bilotechnology, Vol 6 (6), (1988)
Rigby D. W. J. et al, J Mol Biol 113, 237–251, 1977
Sherman D. et al, EMBO J 8, 2717–2725, 1989
Shimkets L. J. et al, Proc Natl Acad Sci USA, 80: 1406–1410 (1983)
Simon R. et al, Bio/Technol. Nov 83, 784–791, 1983
Smith C. L. et al, Methods Enzymol 151, 461–489 (1987)
Schupp T. et al, Gene 64, 179–188, 1988
Schupp T. et al, FEMS Microbiol Letters 36, 237–251, 1986
Wahl G. M. et al, Proc Natl Acad Sci, USA 84, 2160–2164 (1987)
Ward et al, Mol Gen Genet 203, 468–478, 1986

Patent literature

EP-A 0 358 606
U.S. Pat. No. 4,910,140
WO 87/03907

We claim:

1. An isolated DNA molecule that encodes a polypeptide required for the biosynthesis of soraphen A, wherein said DNA molecule specifically hybridizes to SEQ ID NO: 1.

2. The isolated DNA molecule according to claim 1, wherein said DNA molecule is obtained from the genome of a myxobacterium.

3. The isolated DNA molecule according to claim 2, wherein said DNA molecule is obtained from the genome of *Sorangium cellulosum.*

4. The isolated DNA molecule according to claim 1, wherein said DNA molecule comprises SEQ ID NO: 1.

5. An isolated DNA molecule consisting of SEQ ID NO: 1.

6. A prokaryotic vector comprising the isolated DNA molecule according to claim 1.

7. The vector according to claim 6, which is a transformation vector.

8. The vector according to claim 6, which is an expression vector.

9. A prokaryotic host cell comprising the vector according to claim 6.

10. A cosmid clone designated p98/1 and deposited as NRRL B-21255.

* * * * *